United States Patent
Zhang et al.

(10) Patent No.: US 12,090,324 B2
(45) Date of Patent: Sep. 17, 2024

(54) SPINAL CORD STIMULATION FOR DORSAL COLUMN RECRUITMENT OR SUPPRESSION USING ANODIC AND CATHODIC PULSES

(71) Applicant: Boston Scientific Neuromodulation Corporation, Valencia, CA (US)

(72) Inventors: Tianhe Zhang, Studio City, CA (US); Michael A. Moffitt, Solon, OH (US); Que Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 237 days.

(21) Appl. No.: 16/741,171

(22) Filed: Jan. 13, 2020

(65) Prior Publication Data
US 2020/0147390 A1    May 14, 2020

Related U.S. Application Data

(63) Continuation-in-part of application No. 16/738,786, filed on Jan. 9, 2020, now Pat. No. 11,951,314, which
(Continued)

(51) Int. Cl.
  *A61N 1/36* (2006.01)
  *A61N 1/05* (2006.01)
  *A61N 1/372* (2006.01)

(52) U.S. Cl.
  CPC ....... *A61N 1/36132* (2013.01); *A61N 1/0551* (2013.01); *A61N 1/36178* (2013.01); *A61N 1/37211* (2013.01)

(58) Field of Classification Search
  CPC .............. A61N 1/36132; A61N 1/0551; A61N 1/36178; A61N 1/37211; A61N 1/36062;
  (Continued)

(56) References Cited

U.S. PATENT DOCUMENTS

| 4,520,825 A | 6/1985 | Thompson et al. |
| 6,181,969 B1 | 1/2001 | Gord |

(Continued)

FOREIGN PATENT DOCUMENTS

| CN | 202933390 | 5/2013 |
| EP | 2923727 | 9/2015 |

(Continued)

OTHER PUBLICATIONS

U.S. Appl. No. 62/802,998, filed Feb. 8, 2019, Doan et al.
(Continued)

*Primary Examiner* — Gary Jackson
*Assistant Examiner* — Ranjani Mari Sundaresan
(74) *Attorney, Agent, or Firm* — Lewis & Reese, PLLC

(57) ABSTRACT

New waveforms for use in an implantable pulse generator or external trial stimulator are disclosed which mimic actively-driven biphasic pulses, and which are particularly useful for providing sub-perception Spinal Cord Stimulation therapy using low frequency pulses. The waveforms comprise anodic and cathodic pulses which are effectively monophasic in nature, although low-level, non-therapeutic charge recovery can also be used.

17 Claims, 20 Drawing Sheets

Related U.S. Application Data is a continuation-in-part of application No. 16/657,560, filed on Oct. 18, 2019, which is a continuation-in-part of application No. 16/100,904, filed on Aug. 10, 2018, now Pat. No. 10,576,282, said application No. 16/657,560 is a continuation-in-part of application No. 16/460,640, filed on Jul. 2, 2019, said application No. 16/657,560 is a continuation-in-part of application No. 16/460,655, filed on Jul. 2, 2019, now Pat. No. 11,338,127.

(60) Provisional application No. 62/849,642, filed on May 17, 2019, provisional application No. 62/803,330, filed on Feb. 8, 2019, provisional application No. 62/693,543, filed on Jul. 3, 2018, provisional application No. 62/544,656, filed on Aug. 11, 2017.

(58) Field of Classification Search
CPC ............ A61N 1/36146; A61N 1/36175; A61N 1/36128; A61N 1/36135; A61N 1/36185
See application file for complete search history.

(56) References Cited

U.S. PATENT DOCUMENTS

| | | |
|---|---|---|
| 6,246,912 B1 | 6/2001 | Sluijter et al. |
| 6,516,227 B1 | 2/2003 | Meadows et al. |
| 6,560,490 B2 | 5/2003 | Grill et al. |
| 7,603,177 B2 | 10/2009 | Sieracki et al. |
| 7,734,340 B2 | 6/2010 | De Ridder |
| 7,890,182 B2 | 2/2011 | Parramon et al. |
| 8,180,451 B2 | 5/2012 | Hickman et al. |
| 8,224,453 B2 | 7/2012 | De Ridder |
| 8,359,102 B2 | 1/2013 | Alataris et al. |
| 8,364,273 B2 | 1/2013 | De Ridder |
| 8,401,655 B2 | 3/2013 | De Ridder |
| 8,515,546 B2 | 8/2013 | Goddard et al. |
| 8,606,362 B2 | 12/2013 | He et al. |
| 8,620,436 B2 | 12/2013 | Parramon et al. |
| 8,712,533 B2 | 4/2014 | Alataris et al. |
| 8,712,534 B2 | 4/2014 | Wei |
| 8,774,927 B2 | 7/2014 | DeRidder |
| 8,792,988 B2 | 7/2014 | Alataris et al. |
| 8,897,870 B2 | 11/2014 | De Ridder |
| 8,934,981 B2 | 1/2015 | De Ridder |
| 9,259,574 B2 | 2/2016 | Aghassian et al. |
| 9,327,125 B2 | 5/2016 | Alataris et al. |
| 9,333,357 B2 | 5/2016 | Alataris et al. |
| 9,358,391 B2 | 6/2016 | Zhu et al. |
| 9,446,243 B2 | 9/2016 | Marnfeldt et al. |
| 9,462,398 B2 | 10/2016 | DeRidder |
| 9,480,842 B2 | 11/2016 | Alataris et al. |
| 9,511,227 B2 | 12/2016 | Biele et al. |
| 9,511,232 B2 | 12/2016 | Biele et al. |
| 9,526,899 B2 | 12/2016 | Biele et al. |
| 9,550,062 B2 | 1/2017 | Khalil et al. |
| 9,656,077 B2 | 5/2017 | De Ridder |
| 9,656,081 B2 | 5/2017 | Feldman et al. |
| 9,737,718 B2 | 8/2017 | Biele et al. |
| 9,789,252 B2 | 10/2017 | Gerber et al. |
| 2006/0015153 A1 | 1/2006 | Gliner et al. |
| 2006/0173493 A1 | 8/2006 | Armstrong et al. |
| 2008/0319497 A1 | 12/2008 | Griffith et al. |
| 2010/0023090 A1 | 1/2010 | Jaax et al. |
| 2010/0030299 A1* | 2/2010 | Covalin ............... A61B 18/00 607/46 |
| 2010/0191307 A1 | 7/2010 | Fang et al. |
| 2010/0274312 A1 | 10/2010 | Alataris et al. |
| 2011/0054567 A1* | 3/2011 | Lane ............... A61N 1/36034 607/59 |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2012/0172946 A1 | 7/2012 | Alataris et al. |
| 2013/0053923 A1 | 2/2013 | Jaax et al. |
| 2013/0268026 A1 | 10/2013 | Rao et al. |
| 2013/0289665 A1 | 10/2013 | Marnfeldt et al. |
| 2014/0088672 A1* | 3/2014 | Bedenbaugh ........ A61N 1/0529 607/116 |
| 2014/0277251 A1 | 9/2014 | Gerber et al. |
| 2014/0364919 A1* | 12/2014 | Doan ............... A61N 1/36164 607/46 |
| 2015/0005842 A1* | 1/2015 | Lee ............... A61N 1/36071 607/46 |
| 2015/0080982 A1 | 3/2015 | Funderburk |
| 2015/0157861 A1 | 6/2015 | Aghassian |
| 2015/0231402 A1 | 8/2015 | Aghassian |
| 2015/0335893 A1 | 11/2015 | Parker |
| 2015/0360038 A1 | 12/2015 | Zottola et al. |
| 2016/0082265 A1 | 3/2016 | Moffitt et al. |
| 2016/0114166 A1 | 4/2016 | Kaula et al. |
| 2016/0144183 A1 | 5/2016 | Marnfeldt |
| 2016/0158551 A1 | 6/2016 | Kent et al. |
| 2016/0184591 A1 | 6/2016 | Feldman et al. |
| 2016/0271413 A1 | 9/2016 | Vallejo et al. |
| 2016/0317815 A1 | 11/2016 | Doan et al. |
| 2016/0361543 A1 | 12/2016 | Kaula et al. |
| 2016/0367822 A1 | 12/2016 | Parramon |
| 2017/0050035 A1 | 2/2017 | Gupta et al. |
| 2017/0056642 A1 | 3/2017 | Moffitt et al. |
| 2017/0071490 A1 | 3/2017 | Parker et al. |
| 2017/0106197 A1 | 4/2017 | Wechter et al. |
| 2017/0165490 A1 | 6/2017 | Wechter |
| 2017/0173335 A1 | 6/2017 | Min et al. |
| 2017/0189685 A1 | 7/2017 | Steinke et al. |
| 2018/0043172 A1 | 2/2018 | Serrano Carmona |
| 2018/0064943 A1 | 3/2018 | Grill et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0104493 A1 | 4/2018 | Doan et al. |
| 2018/0110992 A1 | 4/2018 | Parramon et al. |
| 2018/0140831 A1 | 5/2018 | Feldman et al. |
| 2018/0272124 A1 | 9/2018 | Kibler et al. |
| 2018/0345022 A1 | 12/2018 | Steinke et al. |
| 2019/0046800 A1 | 2/2019 | Doan et al. |
| 2019/0083796 A1 | 3/2019 | Weerakoon et al. |
| 2019/0175915 A1 | 6/2019 | Brill et al. |
| 2019/0184180 A1 | 6/2019 | Zhang et al. |
| 2019/0209844 A1 | 7/2019 | Esteller et al. |
| 2019/0290900 A1 | 9/2019 | Esteller et al. |
| 2019/0298992 A1 | 10/2019 | Zhang et al. |
| 2019/0329024 A1 | 10/2019 | Kothandaraman et al. |
| 2019/0329025 A1 | 10/2019 | Moffitt et al. |
| 2019/0329039 A1 | 10/2019 | Marnfeldt et al. |
| 2019/0344083 A1 | 11/2019 | Marnfeldt et al. |
| 2019/0366104 A1 | 12/2019 | Doan et al. |
| 2020/0009367 A1 | 1/2020 | Huertas Fernandez et al. |
| 2020/0009394 A1 | 1/2020 | Huertas Fernandez et al. |

FOREIGN PATENT DOCUMENTS

| | | |
|---|---|---|
| WO | 2014/071445 A1 | 5/2014 |
| WO | 2017/106539 | 6/2017 |

OTHER PUBLICATIONS

U.S. Appl. No. 62/860,627, filed Jun. 12, 2019, Esteller et al.
U.S. Appl. No. 16/657,560, filed Oct. 18, 2019, Moffitt et al.
L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).
S. Thomson et al., "The PROCO Randomised Controlled Trial: Effects of Pulse Rate On Clinical Outcomes in Kilohertz Frequency Spinal Cord Stimulation—A Multicentre, Double-blind, Crossover Study," presented at the International Neuromodulation Society (INS) Meeting on May 31, 2017.
E.C. Celik et al., "The effect of low-frequency TENS in the treatment of neuropathic pain in patients with spinal cord injury," Spinal Cord 51:34-337 (2013).

(56) References Cited

OTHER PUBLICATIONS

Y. Maeda et al., "Low frequencies, but not high frequencies of bi-polar spinal cord stimulation reduce cutaneous and muscle hyperalgesia induced by nerve injury," Pain 138:143-152 (2008).

S. Thomson et al., "Neural Dosing and Energy Requirements in Kilohertz Frequency Spinal Cord Stimulation (SCS)," poster presented at the International Neuromodulation Society (INS) Meeting on May 31, 2017.

S. Paz et al., "Improved Efficacy of SCS Implants Using Multiple Waveforms and Field Shape Options," poster presented at the International Neuromodulation Society (INS) Meeting on May 31, 2017.

S. Paz et al., "Evaluation of Customized Field Shape for Subperception SCS in a Case Series of Chronic Pain Patients," poster presented at the North American Neuromodulation Society (NANS) Meeting on Jan. 11-14, 2018.

S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).

J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).

D. R. McNeal, "Analysis of a Model for Excitation of Myelinated Nerve," IEEE Trans. on Biomedical Eng'g 4, pp. 329-337 (1976).

J. T. Rubinstein, "Axon Termination Conditions for Electrical Stimulation," IEEE Trans. on Biomedical Eng'g 40.7, pp. 654-663 (1993).

Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.

Yearwood, Thomas, "Neuropathic Extremity Paid and Spinal Cord Stimulation," Pain Medicine, vol. 7, No. S1, 2006, 6 pages.

\* cited by examiner

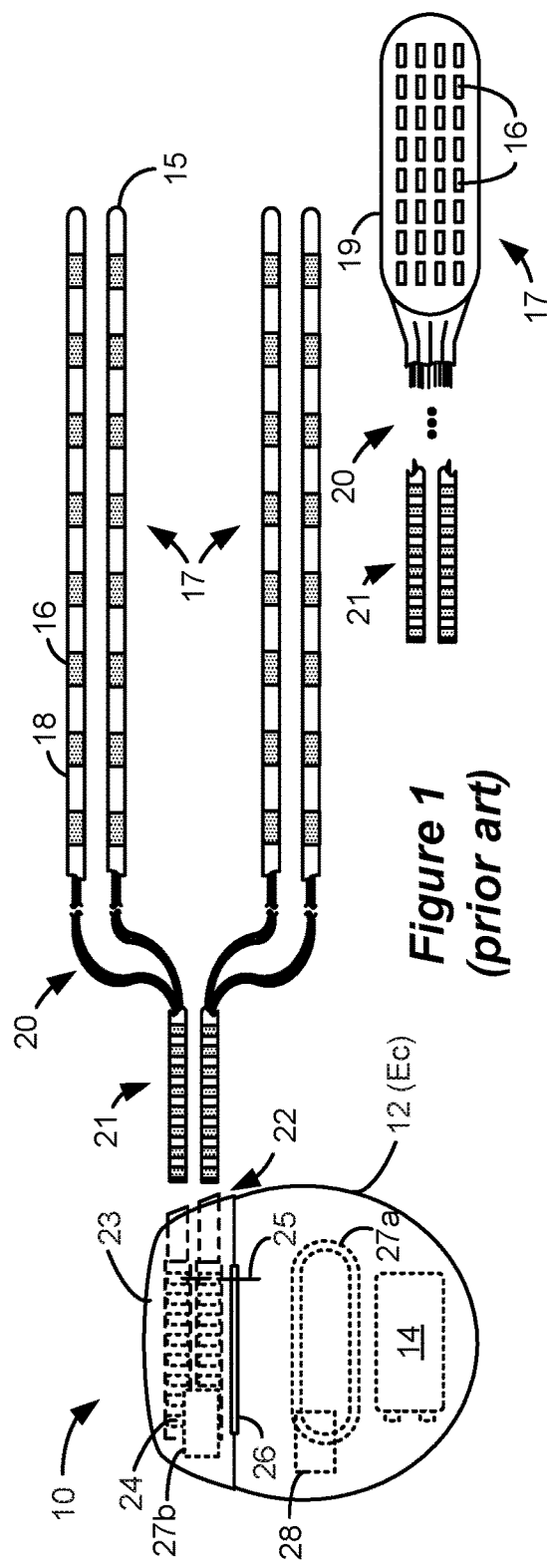
Figure 1 (prior art)
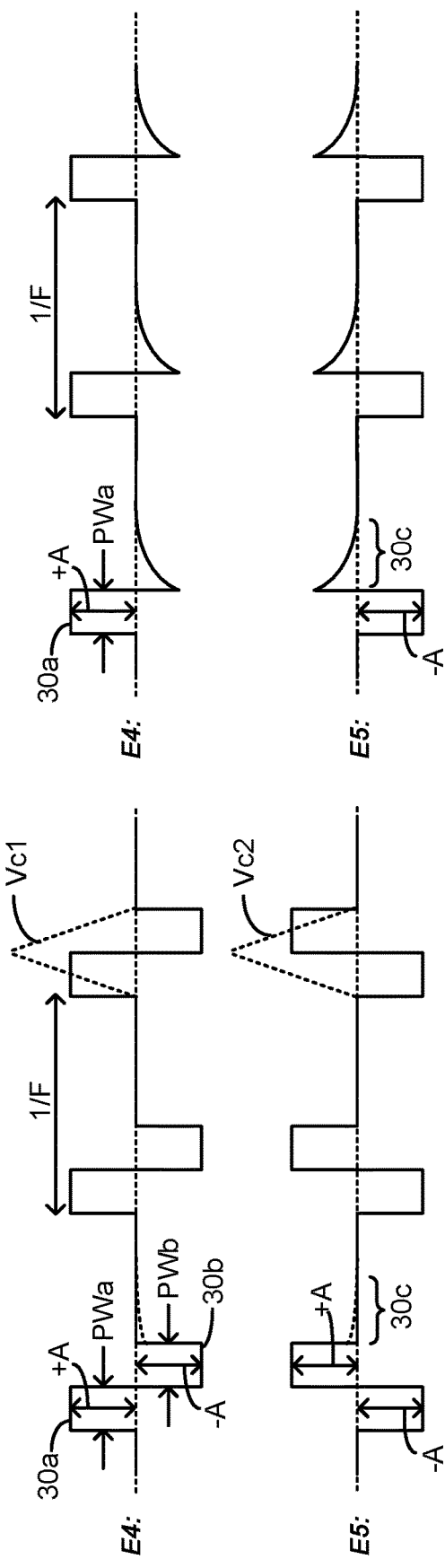
Figure 2A (prior art)
Figure 2B (prior art)

SPINAL CORD STIMULATION FOR DORSAL COLUMN RECRUITMENT OR SUPPRESSION USING ANODIC AND CATHODIC PULSES

CROSS REFERENCE TO RELATED APPLICATIONS

This application is a non-provisional of U.S. Provisional Patent Application Ser. No. 62/849,642, filed May 17, 2019.

This application is also a continuation-in-part of U.S. patent application Ser. No. 16/738,786, filed Jan. 9, 2020, which is a continuation-in-part of U.S. patent application Ser. No. 16/657,560, filed Oct. 18, 2019, which is a continuation-in-part of

- U.S. patent application Ser. No. 16/100,904, filed Aug. 10, 2018, which is a non-provisional application of U.S. Provisional Patent Application Ser. Nos. 62/693,543, filed Jul. 3, 2018, and 62/544,656, filed Aug. 11, 2017;
- U.S. patent application Ser. No. 16/460,640, filed Jul. 2, 2019, which is a non-provisional application of U.S. Provisional Patent Application Ser. No. 62/803,330, filed Feb. 8, 2019; and
- U.S. patent application Ser. No. 16/460,655, filed Jul. 2, 2019, which is a non-provisional application of U.S. Provisional Patent Application Ser. No. 62/803,330, filed Feb. 8, 2019.

Priority is claimed to these above-referenced applications, and all are incorporated by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a typically conductive biocompatible device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer described later with respect to FIG. 5. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses, as shown in FIGS. 2A and 2B. Stimulation parameters typically include the amplitude of the pulses (A; whether current or voltage); the frequency (F) of the pulses; the pulse width (PW) of the pulses (or its individual phases as described below); the electrodes 16 (E) activated to provide such stimulation; and the polarity (P) of such active electrodes, i.e., whether active electrodes are to act as anodes that source current to the tissue or cathodes that sink current from the tissue. These and possibly other stimulation parameters taken together comprise a stimulation program that the IPG 10 can execute to provide stimulation to a patient.

The pulses in FIG. 2A comprise two pulse phases 30a and 30b each actively driven by stimulation circuitry 28 shown in FIG. 3. During the first phase 30a, electrode E4 has been selected as an anode and thus sources a positive current of amplitude +A to the tissue, while electrode E5 has been selected as a cathode and thus sinks a corresponding negative current of amplitude −A from the tissue. However, more than one electrode may act as an anode at a given time, and more than one electrode may act as a cathode at a given time. Stimulation may also occur using the case electrode Ec, as shown in FIG. 3.

The pulses as shown in FIG. 2A, with two actively-driven phases 30a and 30b, are typically known as "biphasic" pulses, with phases 30a and 30b having opposite polarity. (A short interphase period may intervene between the two phases 30a and 30b during which no current flows, although this isn't shown). The use of biphasic pulses are useful in charge recovery, which can be necessary in light of capacitances in the current path established between the selected electrodes, as explained further below. Although not shown, each of the phases 30a and 30b could be broken up into a series of higher-frequency pulses, which is often referred to as a "burst" of pulses, as is well known.

The stimulation circuitry 28 as shown in FIG. 3 includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources. Although not shown, switching matrices can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more anode or cathode electrode nodes at a given time.

The stimulation circuitry 28 is configured by the stimulation parameters, which may be provided to the stimulation circuitry 28 by controller circuitry 29 in the IPG 10. Controller circuitry 29 may comprise a microcontroller, microprocessor, microcomputer, an FPGA, other digital logic structures, etc., which is capable of executing instructions an electronic device. Controller circuitry 29 may comprise a separate component, or may be integrated with an Application Specific Integrated Circuit (ASIC) that includes the stimulation circuitry 28 as well as other circuitry necessary to operate various function of the IPG 10. Proper control of the PDACs $40_i$ and NDACs $42_i$ via the stimulation parameters allows any of the electrodes 16 to act as anodes or cathodes to create a current I of the prescribed amplitude A through a patient's tissue, R, hopefully with good therapeutic effect. In the example shown, and during the first phase 30a in which electrodes E4 and E5 are selected as an anode and cathode respectively, PDAC $40_4$ and NDAC $42_5$ are activated and digitally programmed to produce the desired current, A, with the correct timing (e.g., in accordance with the prescribed frequency F and pulse width PWa). During the second phase 30b (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16. Power for the stimulation circuitry 28 is provided by a compliance voltage VH, as described in further detail in U.S. Patent Application Publication 2013/0289665. Other examples of stimulation circuitries and details of various PDAC and NDAC circuits are disclosed in U.S. Pat. Nos. 6,181,969, 8,606,362, 8,620,436, U.S. Patent Application Publications 2018/0071520 and 2019/0083796. Note that the stimulation circuitry 28 is capable of independently setting the current at any of the electrodes—what is sometimes known as a Multiple Independent Current Control (MICC).

A DC-blocking capacitor Ci 38 is placed in series between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

As noted above, biphasic pulses as shown in FIG. 2A can be useful to recover charge stored on capacitances in the current path and in particular on the DC-blocking capacitors 38. When constant current I is driven during the first phase 30a, the capacitors in the current path (C4 and C5) will store charge at a rate dV/dt=I/C, and thus building a voltage across these capacitors (Vc4 and Vc5). When the polarity of this current is reversed during the second phase 30b, this stored charge is recovered, and the voltage across the capacitors preferably returns to zero before the issuance of the next pulse (i.e., before the next phase 30a). Using biphasic pulses in this manner is sometimes referred to as "active" charge recovery, because the charge stored during the first phase 30a is recovered by a current actively driven by the stimulation circuitry 28 during the second phase 30b. It is usually preferred during active charge recovery that the phases 30a and 30b are charge balanced—that is, that the amount of charge passed during the first phase 30a equal the amount of charge passed during the second phase 30b. This can be achieved by setting the current amplitude and the pulse widths to equal values during both phases (|+A|=|−A|; PWa=PWb). However, this is not strictly necessary, and charge balancing can also be achieved if the product of the amplitude and pulse width is equal for both phases (or more generally if the area under their curves is equal).

Stimulation pulses may also be provided using monophasic pulses followed by the use of passive charge recovery, as shown in FIG. 2B. Such monophasic pulses comprise only a single active phase 30a, which is actively driven as before. Because this phase 30a will charge capacitances in the current path as just described, it is again prudent to recover such charge, but this occurs passively without the stimulation circuitry 28 (i.e., the PDACs and NDACs) driving an active current. Specifically, passive charge recovery switches $41_i$ are provided in the stimulation circuitry 28 (FIG. 3). A switch $41_i$ is coupled between each of the electrode nodes ei 39 and a reference potential. In the depicted example, this reference potential comprises the voltage of the battery 14 (Vbat), although another reference potential can be used. After the first pulse phase 30a is issued, one or more of these switches $41_i$ (all, or at least $41_4$ and $41_5$ whose electrodes nodes e4 and e5 were involved in providing the current during the first phase) are closed during a passive charge recovery period 30c (FIG. 2B). This places the capacitors charged during the first phase in parallel between the reference potential (Vbat), and the patient's tissue, R. As a result, and as shown in FIG. 2B, a current pulse of opposite polarity will flow at each electrode as the capacitors discharge, which current will exponentially decay at a rate depending of the values of the capacitances and the resistances inherent in the IPG's circuitry and the tissue R. Preferably, switches 41, are closed during period 30c for a duration sufficient to effectively recover all charge that was stored on capacitive elements (e.g., capacitors 38) during the first phase 30a. At the end of passive charge recovery period, the switches 41, can again be opened. Passive charge recovery is more fully explained in U.S. Patent Application Publications 2018/0071527 and 2018/0140831.

Note that passive charge recovery can also be used with the biphasic pulses shown in FIG. 2A. Thus, a passive charge recovery period 30c may follow the second actively-driven phase 30b. Even if the actively-driven phases 30a and 30b are designed to be charge balanced, non-idealities may not result in perfect charge balancing, and so providing passive charge recovery during phase 30c can be prudent to assure that charge is fully recovered before the issuance of a next pulse.

FIG. 4 shows an external trial stimulation environment that may precede implantation of an IPG 10 in a patient. During external trial stimulation, stimulation can be tried on a prospective implant patient without going so far as to implant the IPG 10. Instead, a trial electrode array 17' comprising one or more leads (e.g., one or more percutaneous leads 15 or paddle leads 19) are implanted in the patient's tissue 32 at a target location 34, such as within the spinal column as explained earlier. The proximal ends of the leads of the trial electrode array 17' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, the trial electrode array 17' is explanted, and a full IPG 10 and electrode array 17 are implanted as described above; if unsuccessful, the trial electrode array 17' is simply explanted.

Like the IPG 10, the ETS 40 can include one or more antennas to enable bi-directional communications with external devices, explained further with respect to FIG. 5. Such antennas can include a near-field magnetic-induction coil antenna 42a, and/or a far-field RF antenna 42b, as described earlier. ETS 40 may also include stimulation circuitry able to form the stimulation pulses in accordance with a stimulation program, which circuitry may be similar or identical to the stimulation circuitry 28 present in the IPG 10. ETS 40 may also include a battery (not shown) for operational power.

FIG. 5 shows various external devices that can wirelessly communicate data with the IPG 10 and the ETS 40, including a patient hand-held external controller 45, and a clinician programmer 50. Both of devices 45 and 50 can be used to send a stimulation program to the IPG 10 or ETS 40—that is, to program their stimulation circuitries to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 27a or 42a in the IPG 10 or ETS 40. The external controller 45 can also have a far-field RF antenna 47b capable of wirelessly communicating with the RF antenna 27b or 42b in the IPG 10 or ETS 40. The external controller 45 can also have controller circuitry 48 such as a microprocessor, microcomputer, an FPGA, other digital logic structures, etc., which is capable of executing instructions an electronic device. Controller circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 5, computing device 51 is shown as a laptop computer that includes typical computer user interface means such as a screen 52, a mouse, a keyboard, speakers, a stylus, a printer, etc., not all of which are shown for convenience. Also shown in FIG. 5 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 27a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40. If the IPG 10 or ETS 40 includes an RF antenna 27b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or stimulation parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 6. One skilled in the art will understand that the particulars of the GUI 64 will depend on where clinician programmer software 66 is in its execution, which may depend on previous GUI selections the clinician has made. FIG. 6 shows the GUI 64 at a point allowing for the setting of stimulation parameters for the patient's IPG 10 or ETS 40. While GUI 64 is shown as operating in the clinician programmer 50, the user interface of the external controller 45 may provide similar functionality.

Shown to the right are interfaces where specific stimulation parameters can be defined for a stimulation program. Values for stimulation parameters relating to the shape of the waveform (A; in this example, current; PW; F) are shown in a waveform parameter interface 84, including buttons the clinician can use to increase or decrease these values. Stimulation parameters relating to the electrodes 16 (the active electrodes and their polarities), are made adjustable in an electrode parameter interface 86. Electrode parameters are also visible and can be manipulated in a leads interface 92 that displays the electrode array 17 (or 17') in generally their proper position with respect to each other, for example, on the left and right sides of the spinal column (only two leads are shown for simplicity). A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIGS. 2A and 2B, as shown in the leads interface 92, electrode E4 has been selected as the only anode to source current, and this electrode receives X=100% of the specified anodic current, +A. Likewise, electrode E5 has been selected as the only cathode to sink current, and this electrode receives X=100% of that cathodic current, -A. Again, more than one electrode can be selected to act as an anode or cathode at one time, with those electrodes sharing the anodic current +A or cathodic current -A. For example, electrodes E3 and E4 can both be selected to act as anode electrodes, with E3 receiving 30% of +A, and E4 receiving 70% of +A. GUI 64 can include other advanced options not shown as well, which for example allow for setting of a duty cycle (on/off time) for the stimulation pulses, setting a ramp-up time over which stimulation pulses will reach its programmed amplitude (A), options to specify the use of biphasic waveforms and/or passive charge recovery, etc.

SUMMARY

A method is disclosed for programming a spinal cord stimulator device comprising an electrode array with a plurality of electrodes. The method may comprise: programming the spinal cord stimulator device to provide an anodic pulse at an anodic pole in the electrode array during a first duration; and programming the spinal cord stimulator device to provide a plurality of cathodic pulses at cathodic poles in the electrode array during a second duration occurring before or after the first duration, wherein at least two of the cathodic poles are aligned rostral-caudally in the electrode array with respect to the anodic pole, and wherein at least one cathodic pole is aligned medio-laterally in the electrode array with respect to the anodic pole.

In one example, no cathodic pulses are provided to the electrode array during the first duration. In one example, no anodic pulses are provided to the electrode array during the second duration. In one example, the first and second durations do not overlap in time. In one example, the spinal cord stimulator device further comprises a conductive case electrode, and wherein the case electrode provides a cathodic current return for the anodic pulse during the first duration, and wherein the case electrode provides an anodic current return for the cathodic pulses during the second duration. In one example, the method further comprises programming the spinal cord stimulator device to provide a cathodic charge recovery pulse at the anodic pole after the anodic pulse, and programming the spinal cord stimulator device to provide anodic charge recovery pulses at the cathodic poles after the cathodic pulses. In one example, the cathodic charge recovery pulse overlaps with the cathodic pulses during the second duration. In one example, the anodic pulse has an amplitude larger than the cathodic charge recovery pulse, and wherein each cathodic pulse has an amplitude larger than the anodic charge recovery pulses. In one example, the anodic pulse is charge balanced with the cathodic charge recovery pulse at the anodic pole, and wherein each cathodic pulse is charge balanced with the anodic charge recovery pulse at each cathodic pole. In one example, the anodic pulse is programmed in a first timing channel in the spinal cord stimulator device, and wherein the cathodic pulses are programmed in a second timing channel in the spinal cord stimulator device. In one example, a charge of the anodic pulse is equal but opposite of the sum of a charge of the cathodic pulses. In one example, an amplitude of the anodic pulse is equal to a sum of amplitudes of the cathodic pulses. In one example, the cathodic pulses have amplitudes which are equal. In one example, the anodic pole is located at one of the plurality of electrodes. In one example, the cathodic poles are each located at different ones of the plurality of electrodes. In one example, the anodic pole is between the at least two of the cathodic poles aligned rostral-caudally in the electrode array. In one example, at least two cathodic poles are aligned medio-laterally in the electrode array with respect to the anodic pole. In one example, the anodic pole is between the at least two of the cathodic poles aligned medio-laterally in the electrode array. In one example, the anodic pulse and the cathodic pulses comprise a pulse group, and further comprising programming the spinal cord stimulator device to periodically provide a plurality of the pulse groups in the electrode array. In one example, the method further comprises programming the spinal cord stimulator device to move at least some of the pulse groups to new locations in the electrode array. In one example, the spinal cord stimulator device further comprises a conductive case electrode, and wherein the case electrode is further programmed with a cathodic pulse during the second duration. In one example, the spinal cord stimulator device further comprises a conductive case electrode, and wherein the case electrode is further programmed with an anodic pulse during the first duration.

In another example, a method is disclosed for programming a spinal cord stimulator device comprising a plurality of electrodes comprising an electrode array. The method may comprise: programming the spinal cord stimulator device to provide pulses during successive time periods, wherein during each time period pulses are provided to three or more pole locations, wherein the spinal cord stimulator device is programmed to provide a cathodic pulse at one of the pole locations and anodic pulses at two or more of the pole locations during each of the successive time periods, wherein the cathodic pulse is moved to different of the pole locations during different of the successive time periods.

In one example, the three or more pole locations are spaced medio-laterally in the electrode array. In one example, the spinal cord stimulator device further comprises a conductive case electrode, and wherein the case electrode provides a current return during at least some of the successive time periods. In one example, during at least some of the successive time periods the cathodic pulse is not charge balanced with the anodic pulses. In one example, the method further comprises programming the spinal cord stimulator device to provide charge recovery pulses at the pole locations after the cathodic pulse and the anodic pulses during each successive time period. In one example, the cathodic pulse and the anodic pulses completely overlap during each successive time period. In one example, the cathodic pulse and the anodic pulses do not completely overlap during each successive time period. In one example, during each successive time period the cathodic pulse comprises a first charge and the anodic pulses in sum comprise a second charge equal and opposite the first charge. In one example, during each successive time period an amplitude of the cathodic pulse is equal to a sum of amplitudes of the anodic pulses. In one example, during each successive time period the cathodic pulse and the one or more anodic pulses are formed in a single timing channel. In one example, the pulses are formed in different timing channels at each of the different pole locations. In one example, at each pole location the cathodic pulse is charge balanced with the anodic pulses over some number of successive time periods. In one example, at each pole location the amplitude of the cathodic pulse is equal to a sum of amplitudes of the anodic pulses over the number of successive time periods. In one example, during each successive time period the anodic pulses have amplitudes which are equal. In one example, the cathodic pulse during each successive time period is provided at a pole location which is located at one of the plurality of electrodes. In one example, the anodic pulses during each successive time period are provided at pole locations which are each located at different ones of the plurality of electrodes. In one example, the cathodic pulse is moved to a different one of the pole locations during each successive time period. In one example, during each successive time period an amplitude of one of the anodic pulses at the two or more pole locations is larger than an amplitude of the anodic pulses at the other pole locations. In one example, the cathode pulse is provided at the pole location of the larger-amplitude anodic pulse during a next of the successive time periods.

In another example, a method is disclosed for programming a spinal cord stimulator device implanted in a patient tissue comprising an electrode array with a plurality of electrodes. The method may comprise: programming the spinal cord stimulator device to provide at an anodic pole in the electrode array a repeating pattern of first pulses each comprising an anodic pulse phase, wherein the first pulse comprises at least one phase, and wherein the anodic pulse phase occurs during a first of the at least one phases during a first duration; and programming the spinal cord stimulator device to provide at one or more cathodic poles in the electrode array a repeating pattern of a plurality of second pulses each comprising cathodic pulse phase, wherein the second pulses each comprise at least one phase, and wherein the cathodic pulse phase occurs during a first of the at least one phases during a second duration, wherein the first and second pulses are interleaved such that the first and second durations are interleaved in time. This method may be further limited in the manners provided above.

In another example, a method for programming a spinal cord stimulator device implanted in a patient's tissue comprising an electrode array with a plurality of electrodes is disclosed. The method may comprise: programming the spinal cord stimulator device to provide an anodic pulse at an anodic pole in the electrode array during a first duration; programming the spinal cord stimulator device to provide a plurality of cathodic pulses at cathodic poles in the electrode array during a second duration occurring before or after the first duration; and calibrating an amplitude of the anodic pulse, the cathodic pulses, or both of the anodic pulse and the cathodic pulses, so as to elicit a response in the tissue.

In one example, both the anodic pulse and the cathodic pulses are calibrated so as to elicit a response in the tissue. In one example, the amplitude is calibrated so as to elicit a response in the patient's tissue using feedback from the patient. In one example, the amplitude is calibrated so as to elicit a response in the patient's tissue using measurements of neural responses in the patient's tissue. In one example, the response elicited in response to the anodic pulse comprises of depolarization of the patient's tissue, wherein the response elicited in response to the cathodic pulse comprises of depolarization of the patient's tissue. In one example, the anodic pole and the cathodic poles are in predetermined positions with each other in the electrode array. In one example, the method further comprises moving the anodic pole and the cathodic poles in the electrode array in a manner that preserves their pre-determined positions with respect to each other. In one example, no cathodic pulses are provided to the electrode array during the first duration. In one example, no anodic pulses are provided to the electrode array during the second duration. In one example, the first and second durations do not overlap in time. In one example, the spinal cord stimulator device further comprises a conductive case electrode, and wherein the case electrode provides a cathodic current return for the anodic pulse during the first duration, and wherein the case electrode provides an anodic current return for the cathodic pulses during the second duration. In one example, the method further comprises programming the spinal cord stimulator device to provide a cathodic charge recovery pulse at the anodic pole after the anodic pulse, and programming the spinal cord stimulator device to provide anodic charge recovery pulses at the cathodic poles after the cathodic pulses. In one example, the cathodic charge recovery pulse overlaps with the cathodic pulses during the second duration. In one example, the amplitude of the anodic pulse is larger than an amplitude of the cathodic charge recovery pulse, and wherein the amplitude of each cathodic pulse is larger than amplitudes of the anodic charge recovery pulses.

In one example, the anodic pulse is charge balanced with the cathodic charge recovery pulse at the anodic pole, and wherein each cathodic pulse is charge balanced with the anodic charge recovery pulse at each cathodic pole. In one example, the anodic pulse is programmed in a first timing channel in the spinal cord stimulator device, and wherein the cathodic pulses are programmed in a second timing channel in the spinal cord stimulator device. In one example, a charge of the anodic pulse is equal but opposite of the sum of a charge of the cathodic pulses. In one example, the amplitude of the anodic pulse is equal to a sum of the amplitudes of the cathodic pulses. In one example, the amplitudes of the cathodic pulses are equal. In one example, the anodic pole is located at one of the plurality of electrodes. In one example, the cathodic poles are each located at different ones of the plurality of electrodes. In one example, at least two of the cathodic poles are aligned rostral-caudally in the electrode array with respect to the anodic pole. In one example, at least one of the cathodic poles is aligned medio-laterally in the electrode array with respect to the anodic pole. In one example, at least two of the cathodic poles are aligned medio-laterally in the electrode array with respect to the anodic pole. In one example, the anodic pulse and the cathodic pulses comprise a pulse group, and further comprising programming the spinal cord stimulator device to periodically provide a plurality of the pulse groups in the electrode array. In one example, the method further comprises programming the spinal cord stimulator device to move at least some of the pulse groups to new locations in the electrode array. In one example, the spinal cord stimulator device further comprises a conductive case electrode, and wherein the case electrode is further programmed with a cathodic pulse during the second duration. In one example, the spinal cord stimulator device further comprises a conductive case electrode, and wherein the case electrode is further programmed with an anodic pulse during the first duration.

In another example, a method for programming a spinal cord stimulator device comprising a plurality of electrodes comprising an electrode array. The method may comprise: programming the spinal cord stimulator device to provide pulses during different time periods, wherein during each time period pulses are provided to three or more pole locations in the electrode array, wherein the spinal cord stimulator device is programmed to provide a cathodic pulse at one of the pole locations and anodic pulses at two or more of the pole locations during each of the different time periods, wherein the cathodic pulse is moved to different of the pole locations during at least some of the different time periods.

In one example, the different time periods are successive. In one example, the three or more pole locations are spaced medio-laterally in the electrode array. In one example, the spinal cord stimulator device further comprises a conductive case electrode, and wherein the case electrode provides a current return during at least some of the different time periods. In one example, during at least some of the different time periods the cathodic pulse is not charge balanced with the anodic pulses. In one example, the method further comprises programming the spinal cord stimulator device to provide charge recovery pulses at the pole locations after the cathodic pulse and the anodic pulses during each different time period. In one example, the cathodic pulse and the anodic pulses completely overlap during each different time period. In one example, the cathodic pulse and the anodic pulses do not completely overlap during each different time period. In one example, during each different time period the cathodic pulse comprises a first charge and the anodic pulses in sum comprise a second charge equal and opposite the first charge. In one example, during each different time period an amplitude of the cathodic pulse is equal to a sum of amplitudes of the anodic pulses. In one example, during each different time period the cathodic pulse and the one or more anodic pulses are formed in a single timing channel. In one example, the pulses are formed in different timing channels at each of the different pole locations. In one example, at each pole location the cathodic pulse is charge balanced with the anodic pulses over some number of different time periods. In one example, at each pole location the amplitude of the cathodic pulse is equal to a sum of amplitudes of the anodic pulses over the number of different time periods. In one example, during each different time period the anodic pulses have amplitudes which are equal. In one example, the cathodic pulse during each different time period is provided at a pole location which is located at one of the plurality of electrodes. In one example, the anodic pulses during each different time period are provided at pole locations which are each located at different ones of the plurality of electrodes. In one example, the cathodic pulse is moved to a different one of the pole locations during each different time period. In one example, during each different time period an amplitude of one of the anodic pulses at the two or more pole locations is larger than an amplitude of the anodic pulses at the other pole locations. In one example, the cathodic pulse is provided at the pole location of the larger-amplitude anodic pulse during a next of the different time periods.

The invention may also reside in the form of a programed external device (via its control circuitry) for carrying out the above methods, a programmed IPG or ETS (via its control circuitry) for carrying out the above method, a system including a programmed external device and IPG or ETS for carrying out the above methods, or as a computer readable media for carrying out the above methods stored in an external device or IPG or ETS.

BRIEF DESCRIPTION OF THE DRAWINGS

FIG. 1 shows an Implantable Pulse Generator (IPG) useable for Spinal Cord Stimulation (SCS), in accordance with the prior art.

FIGS. 2A and 2B show examples of stimulation pulses producible by the IPG employing active charge recovery and passive charge recovery respectively, in accordance with the prior art.

DETAILED DESCRIPTION

Figure 3:
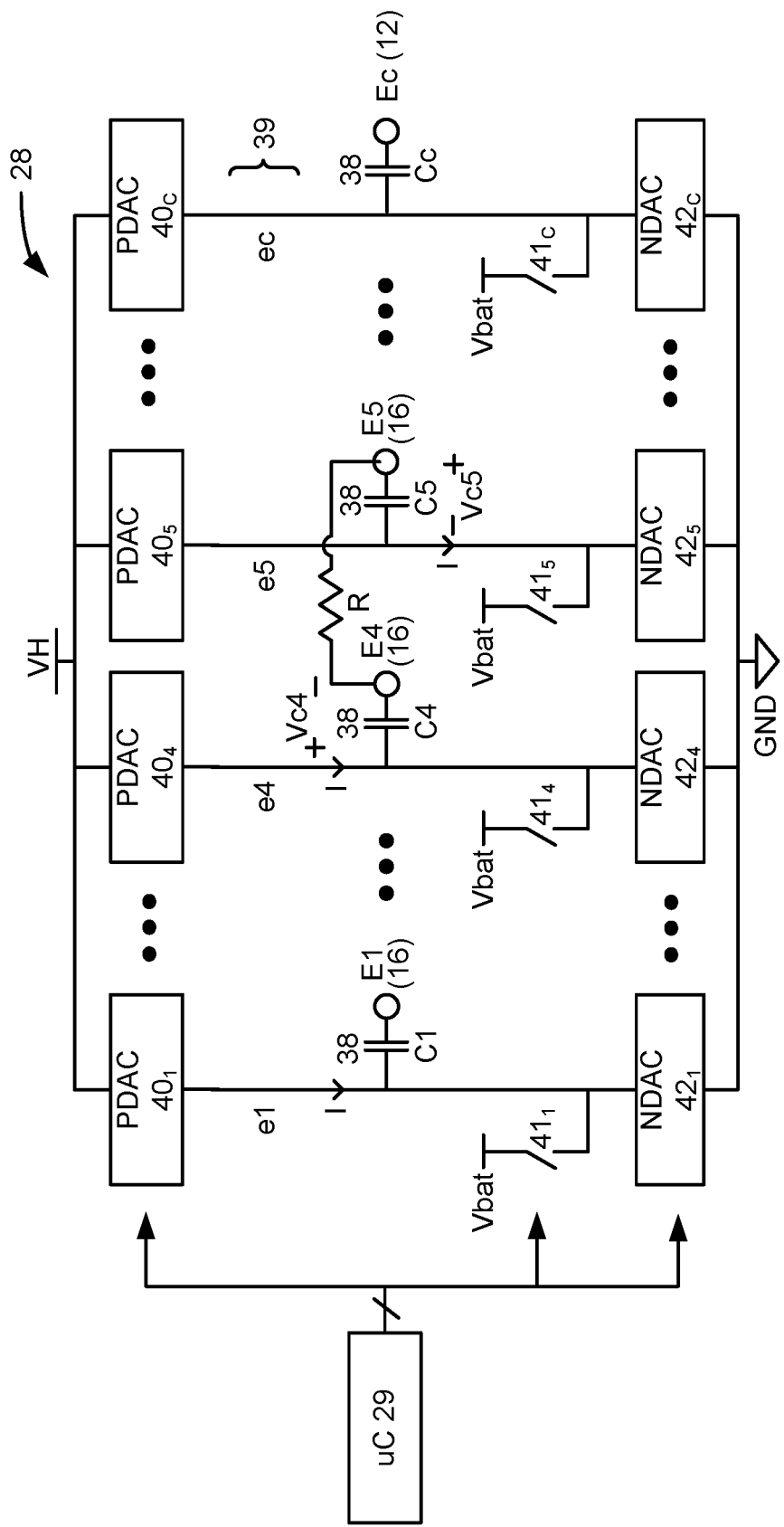
FIG. 3 shows stimulation circuitry used in the IPG to provide stimulation pulses, in accordance with the prior art.
Figure 4:
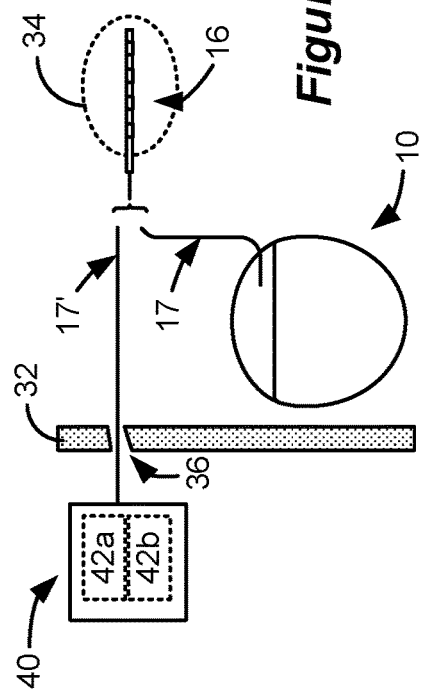
FIG. 4 shows an External Trial Stimulator (ETS) useable to provide stimulation before implantation of an IPG, in accordance with the prior art.

While Spinal Cord Stimulation (SCS) therapy can be an effective means of alleviating a patient's pain, such stimulation can also cause paresthesia. Paresthesia—sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies. Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

In an SCS application, it is desirable to determine a therapeutic stimulation program that will be effective for each patient. A significant part of determining an effective therapeutic stimulation program is to determine a "sweet spot" for stimulation in each patient, i.e., to select which electrodes should be active (E) and with what polarities (P) and relative amplitudes (X %) to recruit and thus treat a neural site at which pain originates in a patient. Selecting electrodes proximate to this neural site of pain can be difficult to determine, and experimentation is typically undertaken to select the best combination of electrodes to provide a patient's therapy. Sweet spot searching to determine the electrodes to use for therapeutic stimulation thereafter is particularly useful in a trial setting after a patient is first implanted with an electrode array, i.e., after receiving their IPG or ETS, but sweet spot searching can also occur at any time during the lifetime of the IPG to optimize therapy.

As described in U.S. Patent Application Publication 2019/0046800 (the '800 Publication), which is hereby incorporated by reference in its entirety, selecting electrodes for a given patient can be even more difficult when sub-perception therapy is used, because the patient does not feel the stimulation, and therefore it can be difficult for the patient to feel whether the stimulation is "covering" his pain and therefore whether selected electrodes are effective. Further, sub-perception stimulation therapy may require a "wash in" period before it can become effective. A wash in period can take up to a day or more, and therefore sub-perception stimulation may not be immediately effective, making electrode selection more difficult.

The '800 Publication discloses that sweet spot searching can therefore preferably occur using supra-perception stimulation, even if the resulting stimulation therapy to be provided following sweet spot searching is sub-perception. Supra-perception therapy by definition allows the patient to feel the stimulation, which enables the patient during sweet spot searching to provide essentially immediate feedback to the clinician whether the paresthesia seems to be well covering his pain without the need for a wash-in period. Further, use of supra-perception stimulation during sweet spot searching ensures that electrodes are determined that well recruit the neural site of a patient's pain. As a result, after the sweet spot search is complete and eventual sub-perception therapy is provided at the determined electrodes, wash in of that sub-perception therapy may not take as long because the electrodes needed for good recruitment have already been confidently determined.

Figure 7:
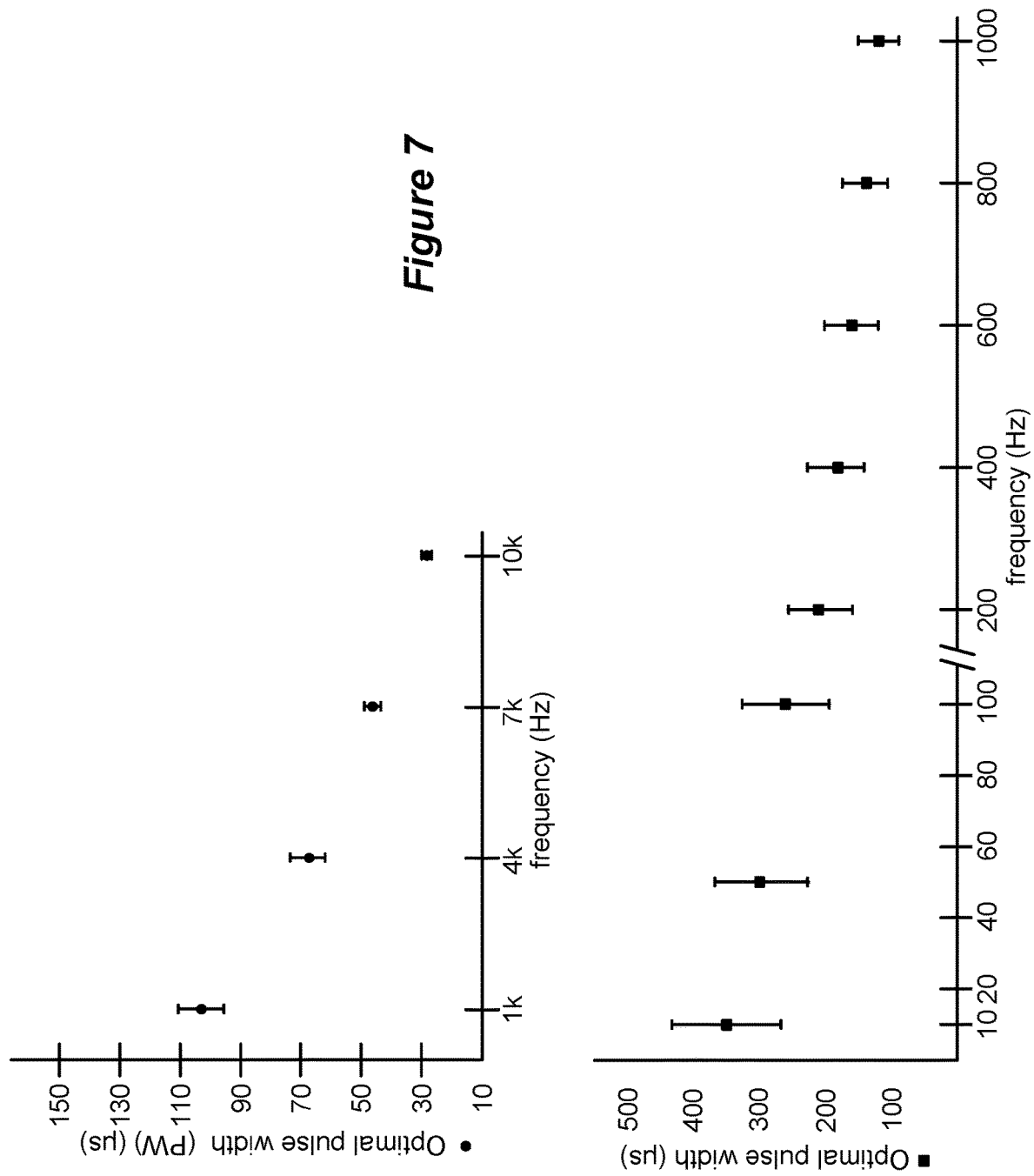
FIG. 7 shows data associating lower frequencies with optimal pulse widths useable to provide sub-perception stimulation in an IPG or ETS.

The '800 Publication explains that effective sub-perception therapy can occur even at lower frequencies (less than or equal to 10 kHz) that use lower amounts of power in the IPG 10 or ETS 40, and that effectiveness at such lower frequencies is achieved when the pulse widths are adjusted to certain values at each frequency. Graphs taken from the '800 Publication are shown in FIG. 7, which shows the relationship between such lower frequencies and pulse widths noticed to provide optimal sub-perception therapy based on empirical testing. The '800 Publication analyzes this data in more depth, including identifying particular relationships (curve fitting) and frequency/pulse width regions indicative of sub-perception effectiveness. The amplitude A of stimulation provided at such frequencies and pulse widths can be tritrated down until sub-perception is reached. The reader is assumed familiar with the '800 Publication, and such details are thus not repeated here.

Figure 8:
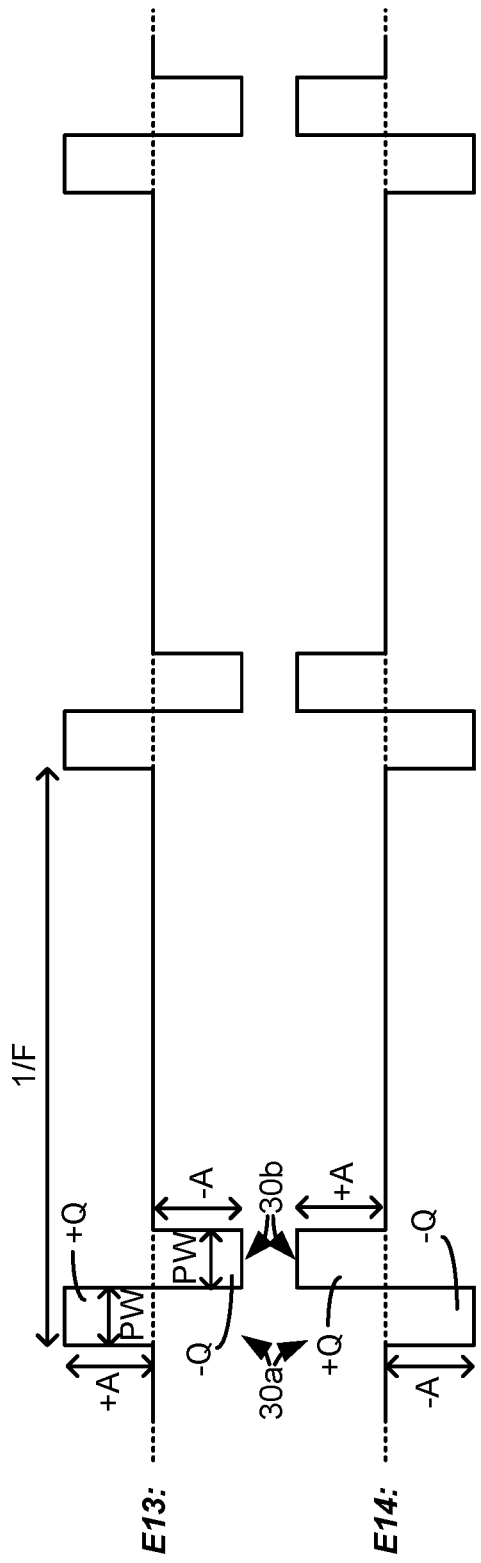
FIG. 8 shows symmetric biphasic pulses that are useful in providing sub-perception therapy at lower frequencies.

Of particular interest in the '800 Publication is the observation that effective sub-perception therapy, can be achieved at very low frequencies (less than or equal to 200 Hz). In the '800 Publication, the pulses used during sub-perception therapy, are preferably symmetric biphasic pulses, such as are shown in FIG. 8. The pulses comprise at least two actively-driven phases 30a and 30b, where the amplitudes A are the same (but of opposite polarity) during each of the phases, and where the pulse widths PW are also equal. It is hypothesized that effectiveness is bolstered because each phase 30a and 30b will tend to actively recruit different neural targets in the patient's tissue. That is, a first group of neural targets is recruited during phase 30a, and a second (possibly overlapping) group of neural targets is recruited during phase 30b. In particular, recruitment would take place most significantly proximate to the cathodes, as neural tissue is generally more easily recruited by cathodic current injection. Thus, generally speaking, in the example of FIG. 8, neural tissue proximate to E14 would be preferentially recruited during phase 30a, and neural tissue proximate to E13 would be preferentially recruited during phase 30b. As such, stimulation coverage is expanded. Furthermore, the use of symmetric biphasic pulses is beneficial because, as noted above, such pulses are charge balanced, hence (ideally) recovering all stored charge by the end of the second phase 30b.

The inventors disclose new means of forming pulses that may be used in an electrode array 17 or 17' to produce much the same effect as the symmetric biphasic pulses shown in FIG. 8. Such new pulses are expected to be particularly useful in providing sub-perception therapy at lower frequencies, similar to what was disclosed in the '800 Publication. That being said, the disclosed pulses may be used for supra-perception therapy, and at higher frequencies if desired. Before introducing such pulses and techniques, a brief discussion of stimulation mechanisms in the spinal cord is provided.

Figure 9:
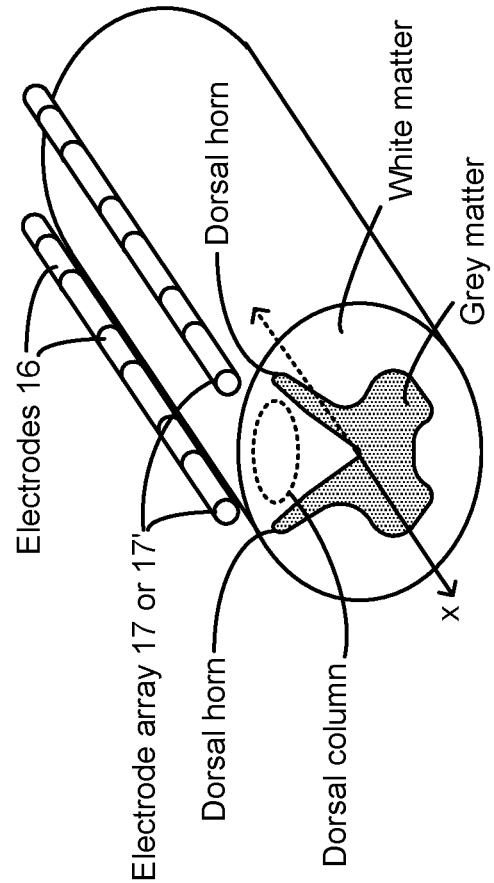
FIG. 9 shows a cross section of a spinal cord which shows the location of dorsal column and dorsal root fibers.

As explained in U.S. Patent Application Publication 2015/0151125 and shown in FIG. 9, a typical transverse section of the spinal cord will include a central "butterfly" shaped central area of gray matter (neuronal cell bodies) substantially surrounded by an ellipse-shaped outer area of white matter (myelinated axons). The dorsal horns are the dorsal portions of the "butterfly" shaped central area of gray matter, which includes neuronal cell terminals, neuronal cell bodies, dendrites, and axons. Conventional SCS programming has as its therapeutic goal maximal stimulation (i.e., recruitment) of dorsal column fibers that run in the white matter along the longitudinal axis of the spinal cord and minimal stimulation of other fibers that run perpendicular to the longitudinal axis of the spinal cord (dorsal root fibers, predominantly). The white matter of the dorsal column includes mostly large myelinated axons that form afferent fibers.

While fibers in the dorsal column run in parallel to the long axis x of the spinal cord (i.e., a rostral-caudal direction), fibers in the dorsal horn can be oriented in many directions, including perpendicular to the long axis of the spinal cord. Dorsal horn fibers and dorsal column fibers have different responses to electrical stimulation. The strength of stimulation (i.e., depolarizing or hyperpolarizing) of the dorsal column fibers is described by the so-called "activating function" $d^2V/dx^2$, which can be determined by taking a second-order spatial derivative of the voltage (V) in the tissue along the longitudinal axis (x) of the spine, because dorsal columns that propagate past the stimulation electrodes are more likely to be activated along the axon. This is partially because the large myelinated axons in dorsal column are primarily aligned longitudinally along the spine. On the other hand, the likelihood of generating action potentials in dorsal horn fibers and neurons is better described by dV/dx (otherwise known as the electric field, E), because dorsal horn fibers and neurons, often constrained to being directly underneath the electrode, may be more likely to respond at dendrites and terminals. Thus, the dorsal horn "activating function" is proportional not to the second-order derivative, but to the first-order derivative of the Voltage along the fiber axis. Accordingly, distance from the electrical field locus affects the dorsal horn activating function less than it affects the dorsal column activating function. See generally D. R. McNeal, "Analysis of a Model for Excitation of Myelinated Nerve," IEEE Trans. on Biomedical Eng'g 4, pp. 329-37 (1976); J. T. Rubinstein, "Axon Termination Conditions for Electrical Stimulation," IEEE Trans. on Biomedical Eng'g 40.7, pp. 654-63 (1993).

Figure 10:
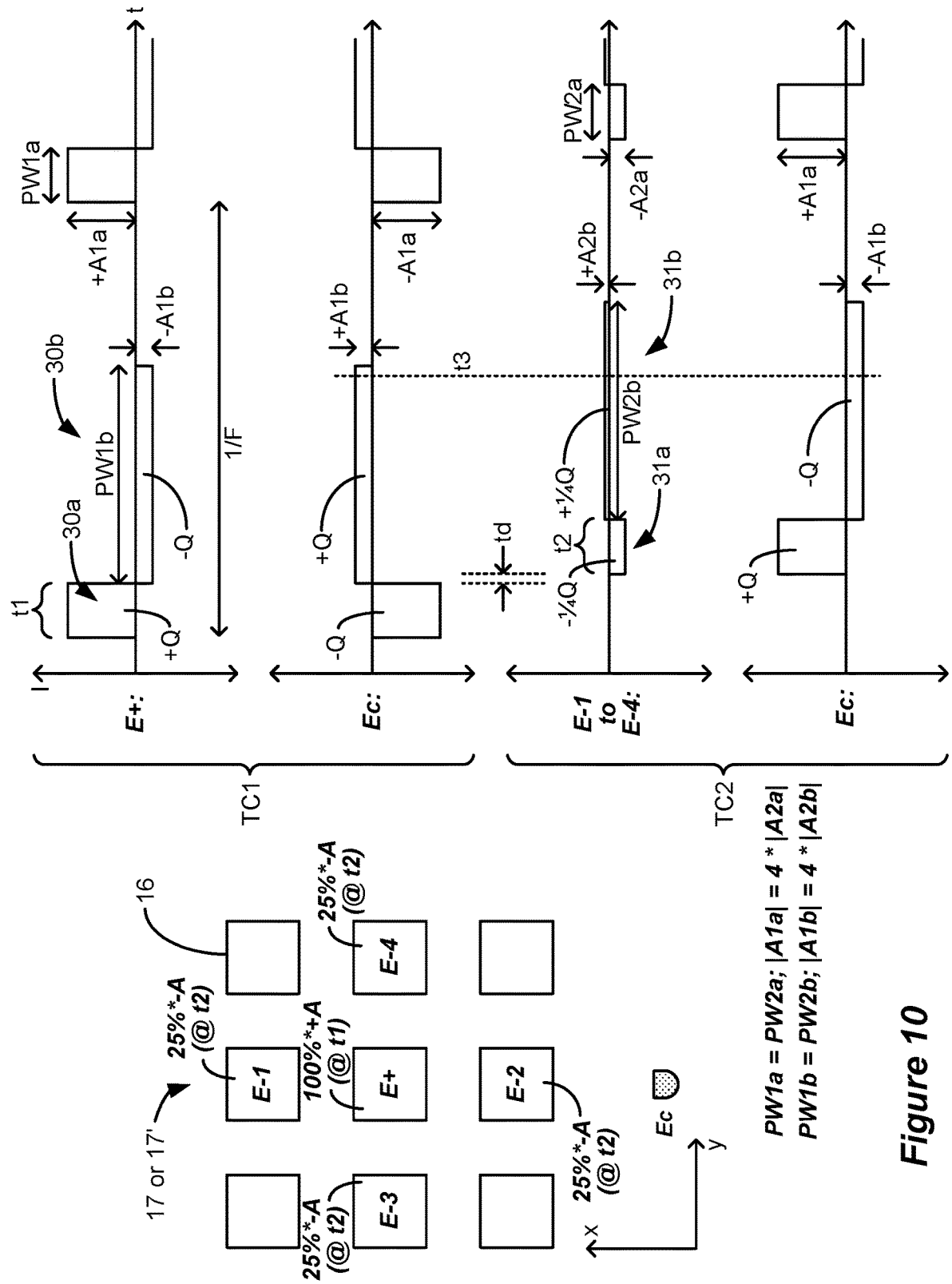
FIG. 10 shows an example of pulses that can be provided to an electrode array to mimic the response of the symmetric biphasic pulses of FIG. 8, which uses a central anodic pulse issued at a first time, and cathodic pulses at adjacent electrodes issued at a second time.

New pulsing techniques disclosed herein employ teachings as learned from the dorsal column activating function $d^2V/dx^2$ to promote or suppress activation of neural targets in the dorsal column. A first example is shown in FIG. 10, which illustrates pulses provided to various electrodes 16 in the electrode array 17 or 17' (hereinafter referred to as array 17 for simplicity). In the example shown, the array 17 is two dimensional, and includes three rows (arranged rostro-caudally; x) and three columns (arranged medio-laterally) of electrodes 16. This can be achieved by using either a paddle lead 19 or a plurality of percutaneous leads 15 (see FIG. 1), although the particular details of the leads are not shown in FIG. 10 for simplicity.

The electrodes in this example are activated to form a cross pattern, with an anodic pulse being provided to a central electrode at time t1 during a first phase 30a, and cathodic pulses being provided to surrounding electrodes E-1, E-2, E-3, and E-4 at a time t2 during a first phase 31a. Time periods t1 and t2 may be separated by a small gap in time (td) which may be 10 microseconds or so. The anodic pulse provided during time period t1 is shown as having an amplitude of +A1a and a pulse width of PW1a, while the cathodic pulses during time period t2 are shown as having an amplitude of −A2a and a pulse width of PW2a. In this example, the cathodic pulses are smaller in amplitude than the anodic pulse; that is, |A2a| is smaller than |A1a|. There are a couple of reasons why this is desirable. First, as noted above, neural tissue is generally more sensitive to (more easily recruited by) cathodic pulses, and thus the amplitude of the cathodic pulses can be smaller than the anodic pulses. For example, the amplitude required for an anodic pulse to recruit neural tissue may be two to four times as large as a similar cathodic pulse. In this example, the amplitude of the anodic pulse is four time the amplitude of the cathodic pulses (i.e., |A1a|=4*|A2a|). Adjusting the amplitudes of the anodic and cathodic pulses in the fashion is also useful as it allows a single current of amplitude A to be specified, such that 100%*+A can be provided to central electrode E+, and 25*-A being provided to each of the four cathode electrodes E-1 to E-4 (which effectively sets |A1a|=4*|A2a|).

The pulses are preferably charge balanced at each electrode, and in this respect the anodic pulse at the anodic electrode E+ during t1 (30a) is followed by an opposite polarity cathodic pulse during a second phase 30b of amplitude −A1b. Preferably, this cathodic pulse is provided merely for the purpose of charge recovery, and would be lower than the amplitude of the anodic pulse (i.e., |A1b|>|A1a|). Most preferably, the amplitude −A1b is low enough in amplitude to not recruit neural tissue, and in this respect the anodic pulse provided during t1 is effectively monophasic. To provide charge recovery, and because amplitude is −A1b is low, the pulse width during phase 30b, PW1b must be made relatively long, such that |A1a|*PW1a=|A1b|*PW1b.

The pulses at each of the cathode electrodes E-1 to E-4 are also preferably charge balanced, and so the cathodic pulses provided during t2 (31a) are followed by opposite polarity anodic pulses during a second phase 31b of amplitude +A2b. Again, these anodic pulses are preferably provided for charge recovery, and would be lower than the amplitude of the cathodic pulse (i.e., |A2a|>|A2b|), with amplitude +A2b being low enough to not recruit neural tissue, such that the cathodic pulses provided during t2 are effectively monophasic. Again, for charge balancing, the pulse width during phase 31b, PW2b, must be made relatively long, such that |A2a|*PW2a=|A2b|*PW2b. A short duration residual "touch up" phase may be delivered to account for any remaining imperfect charge balance, due for example to charge species diffusion during the stimulation and recovery pulses, immediately following the anodic recharge phase PW2b.

In the example shown, the pulse widths of the anodic pulse during t1 and the cathodic pulses provided during t2 are equal (PW1a=PW2a), as are the pulse widths of the active charge recovery periods that follow (PW1b=PW2b). This is however not strictly necessary, and these various pulses phases can have different pulse widths. Furthermore, charge recovery can be passive during second pulse phases 30b and 31b. Passive charge recovery was discussed earlier and isn't shown for convenience.

The therapeutically-significant pulse phases 30a and 31a in one example are issued in a manner that provides sub-perception therapy for the patient, and thus the amplitudes used during the phases (A1a, A2a) may be titrated down accordingly. Further, the pulses are issued at a frequency F, which in one example may comprise pulses of relatively low frequency (e.g., 10 kHz or less, 1 kHz or less, or even 200 Hz or less), as was taught useful for sub-perception stimulation in the '800 Publication discussed above. However, the disclosed pulsing scheme may also be used for supra-perception stimulation, and at any desired frequency deemed useful for a particular patient.

In this example, the case electrode Ec is preferably used as a current return, and in this regard the pulses provided to the electrode array 17 are what is known in the industry as monopolar. For ease of illustration, the return currents at the case electrode Ec is shown distinctly for the anodic pulse and the cathodic pulses. Thus, at the top of FIG. 10, it is seen that the current at Ec simply comprises the current as issued at the single anode electrode E+, but with opposite polarity. At the bottom of FIG. 10, the current at Ec must recover the current provided from the four cathode electrodes E-1 to E-4, and so is of opposite polarity but with four times the amplitude. While these return currents are shown distinctly, in reality (because there is only one case electrode), these current would sum at the case electrode. For example, if it is assumed that |A1b|=4*|A2b| during the second pulse phases 30b and 31b at time t3, the current at the case electrode Ec would be zero.

In one example, the anodic pulses at E+ and the cathodic pulses E-1 to E-4 are formed independently two different timing channels (TC1 and TC2) in the IPG or ETS. Pulse arbitration could be turned off at the case electrode thus allowing the return currents to sum at the case electrode. However, it is not strictly necessary to use different timing channels to form the pulses. Instead, a single, more complex timing channel could be used, such as by using the IPG architecture and pulse definition circuitry as disclosed in U.S. Patent Application Publication 2018/0071513 for example.

To summarize in one example, FIG. 10 shows a method for programming a spinal cord stimulator device implanted in a patient tissue comprising an electrode array with a plurality of electrodes. This may comprise programming the spinal cord stimulator device to provide at an anodic pole (E+) in the electrode array a repeating pattern of first pulses each comprising an anodic pulse phase (30a), wherein the first pulse comprises at least one phase (30a and 30b), and wherein the anodic pulse phase occurs during a first of the at least one phases during a first duration; and programming the spinal cord stimulator device to provide at one or more cathodic poles (E-1 through E-4) in the electrode array a repeating pattern of a plurality of second pulses each comprising cathodic pulse phase (31a), wherein the second pulses each comprise at least one phase (31a and 31b), and wherein the cathodic pulse phase occurs during a first of the at least one phases during a second duration, wherein the first and second pulses are interleaved such that the first and second durations (during 30a and 30b) are interleaved in time.

Figure 11A:
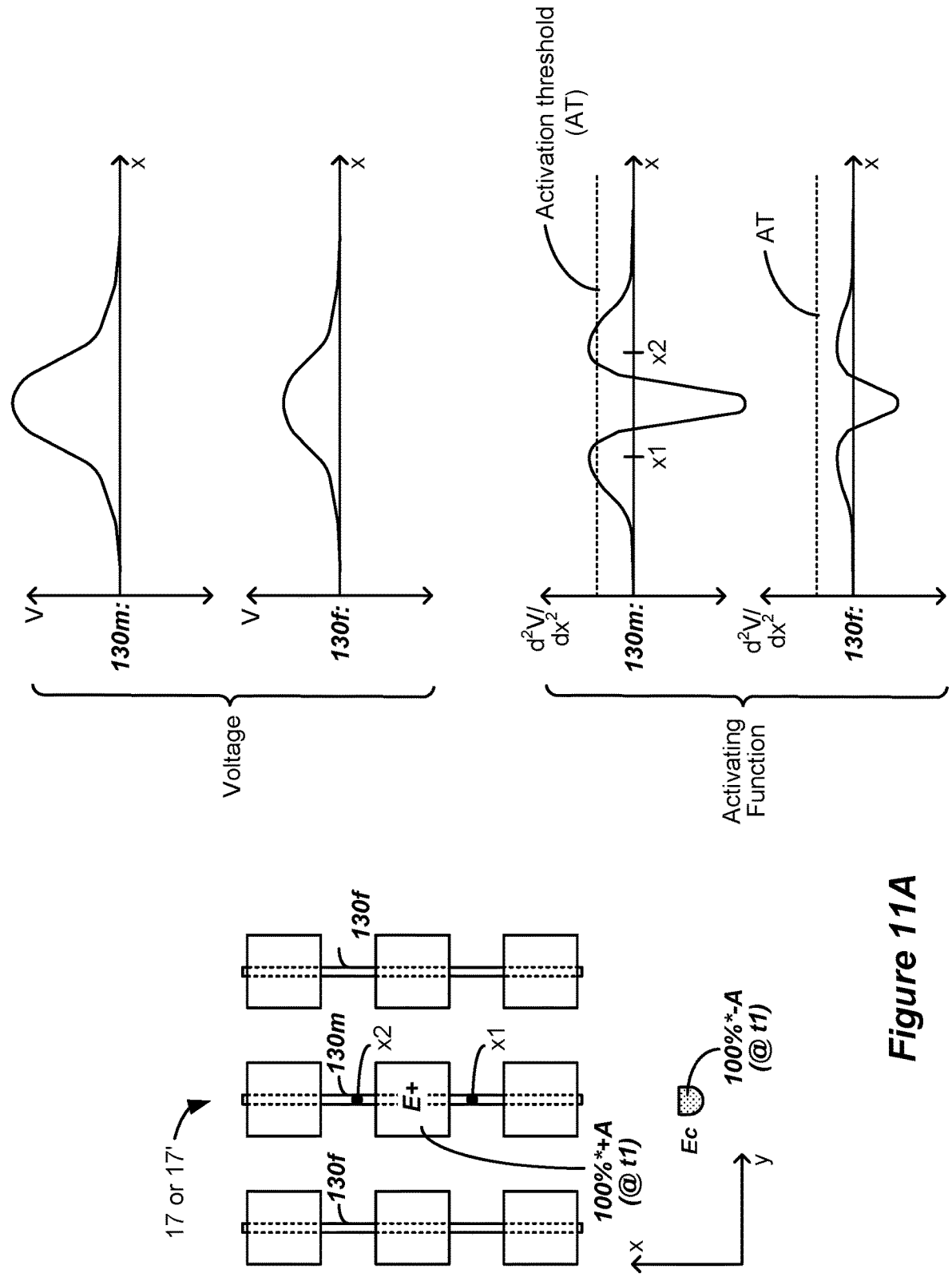
FIGS. 11A and 11B respectively show the effect of neural recruitment of dorsal fibers during the anodic pulse and the cathodic pulses.
Figure 11B:
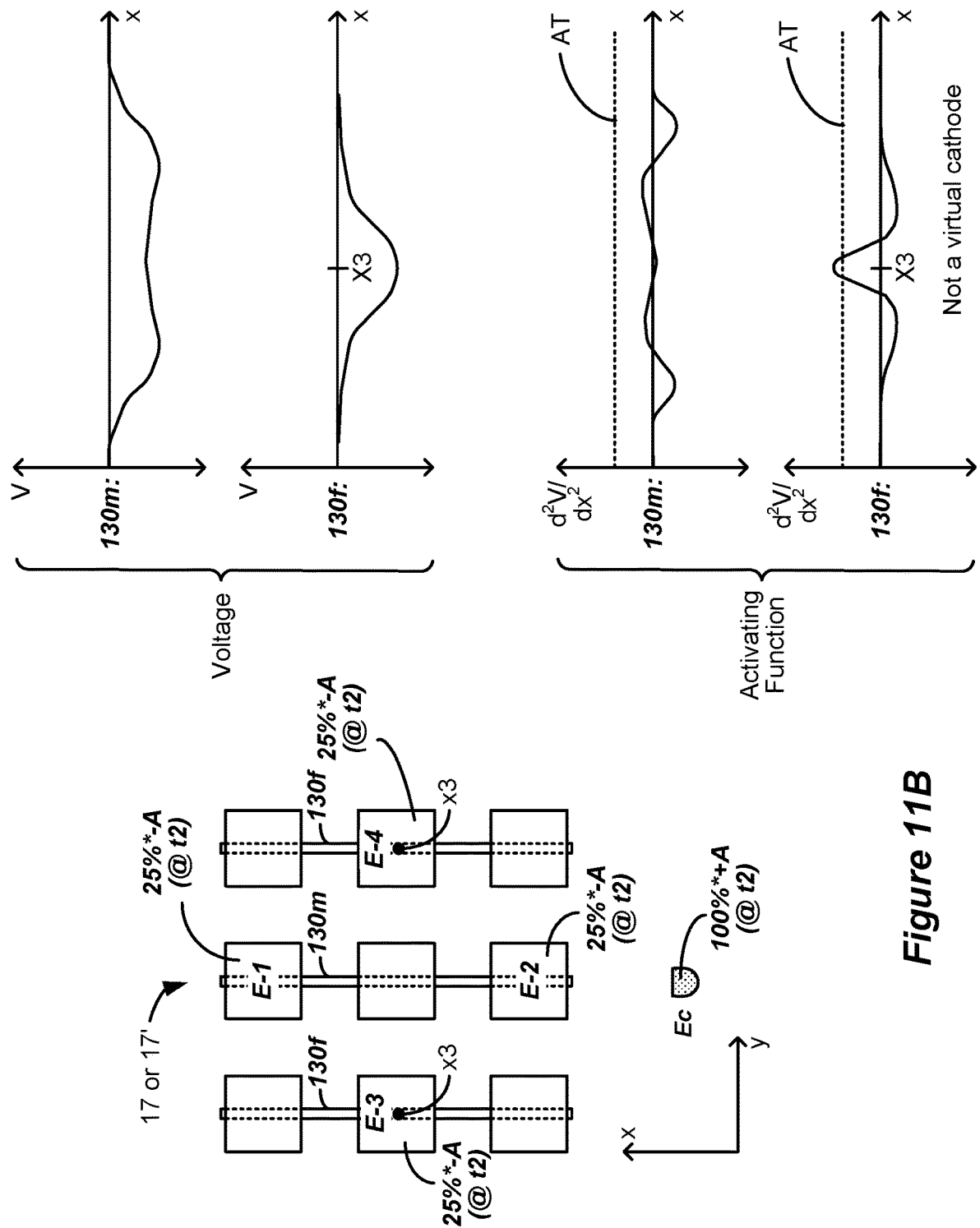

FIGS. 11A and 11B respectively explain what happens during issuance of the pulses at times t1 and t2, and how stimulation in the dorsal column is promoted or suppressed. Such promotion or suppression can be understood by review of the dorsal column fibers beneath the relevant electrodes, as assisted by review of the relevant activating function $d^2V/dx^2$. In this regard, tissues beneath the electrodes are labeled in FIGS. 11A and 11B as 130m and 130f, where "m" refers to the fibers in the middle of the array, and "f" refers to fibers flanking the middle from a medio-lateral perspective (along axis y). Such tissues 130m and 130f would normally contain many dorsal column axons, which as noted earlier are aligned in the x (rostral-caudal) direction.

FIG. 11A shows the anodic pulse at electrode E+ at time t1. The top of FIG. 11A shows the voltages that occur along the x axis at the middle fibers 130m and the flanking fibers 130f. Because E+ is anodic, a positive voltage V will form in the tissue relative to the farther away case electrode Ec. This voltage will be at a maximum along the axis of the middle fibers 130m at the position that underlies the anode electrode E+, and will fall away to smaller values at further distances. The voltage along the axis of the flanking fibers 130f will have this same basic shape, but will be smaller in amplitude as these flanking fibers are farther away from the anode electrode.

The bottom of FIG. 11A shows the shape of the activating function that results along axes 130m and 130f, which as discussed above is determined by taking the second-order derivative of the voltage, i.e., $d^2V/dx^2$. Also shown on the graphs of the activating function is an activation threshold (AT), which can be used to predict depolarization of the underlying tissue. As is known, if the activating function exceeds AT, the tissue will depolarize and fire at those locations; at negative values tissue activation is suppressed. Looking at the activating function along fibers 130m, it is seen that the function exceeds AT above and below the anode electrode E+, and peak points x1 and x2 are denoted. Thus, dorsal column fibers 130m are recruited. Because stimulation tends to preferentially occur proximate to cathodes, x1 and x2 (and regions along 130m that exceed AT) may be referred to as virtual cathodes, despite no cathodic stimulation actually occurring at time t1. By contrast, looking at the activating function along fibers 130f, it is seen that the function does not exceeds AT at any point, owing to the lower amplitude voltages at these locations. Thus, dorsal column tissue is thus not recruited along fibers 130f during the anodic pulse during t1.

It may be beneficial to calibrate an amplitude (+A1a, FIG. 10) of the anodic pulse at anode electrode E+ to ensure that a response is elicited in the tissue, e.g., such that the activating function exceeds the activation threshold AT. Such calibration can occur in different manners. For example, calibration can comprise providing anodic pulses of different amplitudes to the patient, and receiving subjective feedback from the patient about each amplitude's effectiveness at addressing a symptoms of the patient (e.g., pain). Such subjective feedback can also include the determination of various thresholds. For example, the amplitude can gradually be increased until the patient reports feeling the stimulation, thus establishing a paresthesia threshold. The amplitude may also be increased beyond this, for example to the point where the patient can no longer tolerate the stimulation, thus establishing a discomfort threshold.

Calibration can also employ objective measurables. For example, neural responses generated in the patient's neural tissue in response to different amplitudes of anodic stimulation can be measured to gauge whether the patient's tissue has experienced depolarization, and hence whether the activation threshold AT has been exceeded. In one example, neural responses can be gauged by sensing an Evoked Compound Action Potential (ECAP) at one or more of the IPG 10's electrodes 16. Sensing of ECAPs in an IPG is described in U.S. Patent Application Publication Nos. 2017/ 0296823, 2020/0155019 and 2020/0305744, which are incorporated herein by reference. In one example, calibration can occur by verifying an amplitude that is sufficient to evoke an ECAP of a sufficient magnitude or energy. Calibration of the amplitude of the anodic pulses can occur during a testing or "fitting" procedure, as is well known.

FIG. 11B shows the cathodic pulses at electrodes E-1 to E-4 at time t2. The top of FIG. 11B again shows the voltages that occur along the middle fibers 130m and the flanking fibers 130f. Because the pulses are cathodic, negative voltages will form in the tissue, and these voltages will generally be smaller than for the anodic pulse (FIG. 11A) as the cathodic pulses are (preferably) of lower amplitudes as discussed above. The voltage along the x axis of the middle fibers 130m will peak (negatively) at the locations of electrodes E-1 and E-2 that receive cathodic pulses, and will minimize (e.g., at the position of E+ during t1) between these peaks. This minimizes, or flattens, the activating function between the peaks as shown at the bottom of FIG. 11B, such that activation threshold AT is not exceeded at the middle fibers 130m. As a result, dorsal column fibers 130m are not recruited during time t2. In effect, the cathodic stimulation at electrodes E-1 and E-2 suppresses neural recruitment at fibers 130m at time t2.

The voltage along the x axes of the flanking fibers 130f will generally peak (negatively) at the locations of active cathode electrodes E-3 and E-4 (x3). (Some amount of voltage from E-1 and E-2 may couple to 130f, but this would be relatively minor and so is not shown). The resulting activating function thus will peak at these locations along 130f, i.e., at x3, and as shown at the bottom of FIG. 11B can exceed the activation threshold AT, meaning that dorsal column tissue will be recruited proximate to these points x3. In short, dorsal column fibers 130f are depolarized during time t2.

As was true with the anodic pulse (FIG. 11A), it may be beneficial to calibrate an amplitude of the cathodic pulses to ensure that a response is elicited in the tissue, e.g., such that the activating function exceeds the activation threshold AT to cause depolarization. Again, such calibration can occur (e.g., during a testing or fitting procedure) by receiving subjective feedback from the patient in response to different amplitudes, determining various thresholds, or by measuring the neural responses generated in the patient's neural tissue (e.g., by detecting ECAPs), as discussed earlier. Calibration of the amplitudes of the cathode electrodes E-1 to E-4 can occur individually, or the amplitudes of the cathode electrodes can be adjusted until these cathodes in sum produce a desired response.

The overall effect when FIGS. 11A and 11B are considered is that dorsal column fibers 130m are recruited during time t1, while fibers 130f are recruited during time t2. Such recruitment is similar in nature to the symmetric biphasic waveforms provided in FIG. 8, where recruitment of dorsal column fibers at a first location (i.e., proximate to E14) are recruited during a first pulse phase 30a, and where recruitment of dorsal column fibers at a second location (i.e., proximate to E13) are recruited during a second pulse phase 30b. Thus, the new pulsing technique should produce similar results, and in particular have similar beneficial effects for sub-perception stimulation at lower frequencies.

Although not depicted, it should be understood that the anodic and cathodic pulses can be varied in time. For example, the cathodic pulses (e.g., FIG. 11B) can occur at time t1, while the anodic pulse occurs at time t2. This still works a selective recruitment of dorsal column fibers 130m and 130f at different points in time.

Figure 12B:
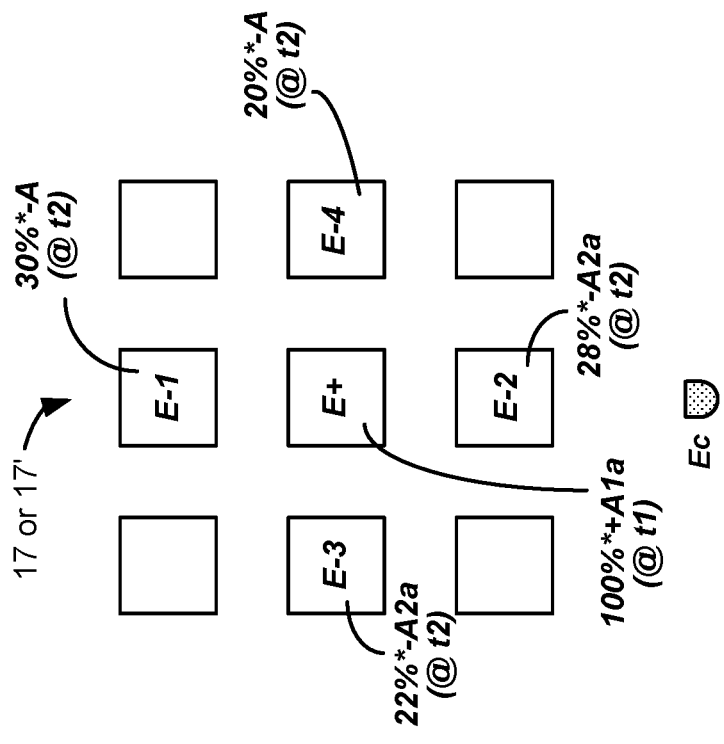
FIGS. 12A-12F show variations to the pulsing technique described in FIGS. 10-11B.
Figure 12A:
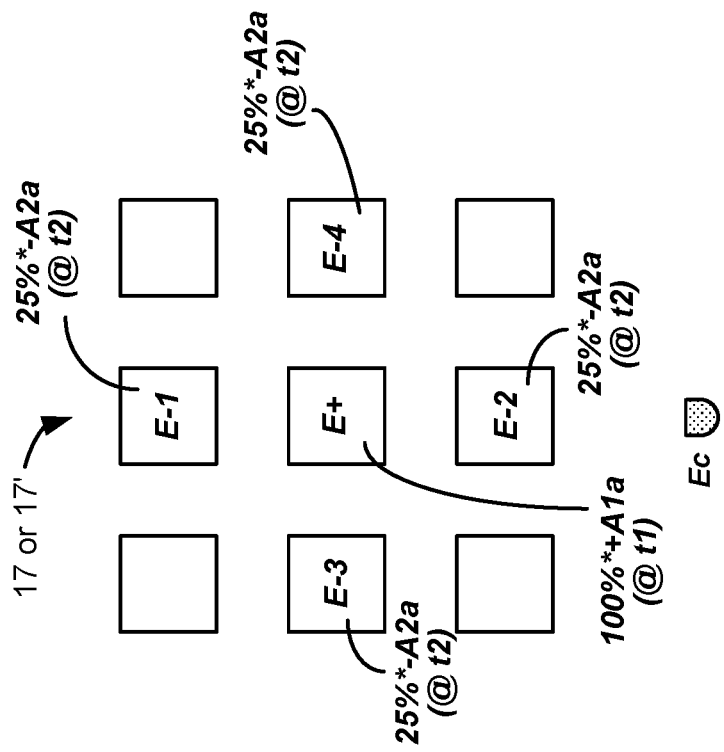
Figure 12D:
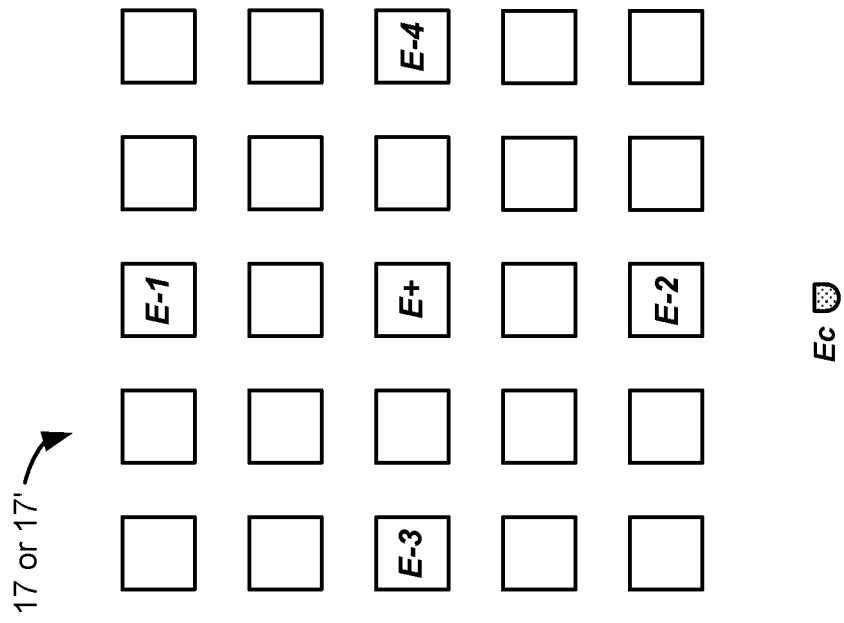
Figure 12C:
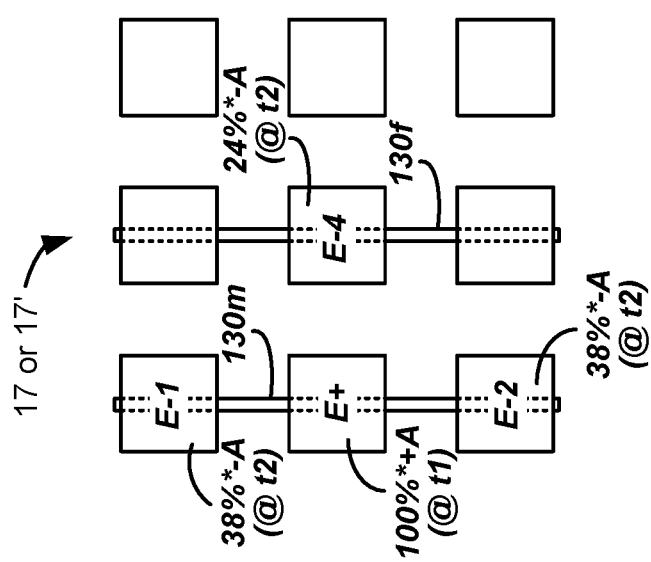

FIGS. 12A through 12C show effective variations to the pulsing sequence described in FIG. 10. FIG. 12A shows that the amplitude of the anodic pulse at E+ during t1 need not have any relationship to the amplitude of the cathodic pulses provided at time t2. Thus, the current provided to the single anodic electrode E+ during t1 can be set to A1a, while the total current provided to the cathodic electrodes E-1 through E-4 during t2 can be set to A2a, with the cathodic electrodes sharing this total current A2a. IN this example, the cathodic electrodes share current A2a in equal proportions (25%*–A2a).

FIG. 12B shows that the current during time t2 can be distributed to the cathodic electrodes E-1 through E-4 in different proportions. In this example, cathodic electrode E-1 receives 30% of the total cathodic current (A in this example), while cathodic electrodes E-2 through E-4 receive 28%, 22%, and 20% of this current respectively. Splitting the cathodic current in unequal proportions can be particularly useful if certain of these electrodes are closer to or farther from the dorsal column fibers that are being stimulated. Closer electrodes better coupled to the dorsal column may require lower amounts of current, while further electrodes more poorly coupled may require higher amounts of current. Techniques for determining the extent of coupling of the electrodes to the spinal cord, and resulting adjustment of the stimulation current received at each electrode, are discussed further in U.S. Patent Application Publication 2020/0230410.

Although not depicted, note that it is not strictly necessary that the cathodic electrodes E-1 through E-4 receive in sum 100% of the cathodic current. Although not shown, the case electrode Ec can receive a remaining amount of the cathodic current if desired. For example, 90% of the cathodic current can be shared by the cathodic electrodes, with the case electrode Ec receiving the remaining 10%. This is also true for the anodic electrode E+, which may also share current with the case electrode Ec.

FIG. 12C shows that it is not strictly necessary that both cathode electrodes medio-laterally flanking the anode electrode E+ receive a cathodic current. In FIG. 12C, the anode electrode E+ is at the edge of the array, and thus there is no cathode electrode E-3 to the left. Nonetheless, cathode electrodes E-1 and E-2 are still provided rostro-caudally, and cathode electrode is still provided medio-laterally (to the right). As such, fibers 130m under the anode electrode E+ will be recruited during t1, while fibers 130f under E-4 will be recruited during time t2. Cathode electrodes E-1 and E-2 as before will act to suppress activation of fibers 130m during t2. In the example of FIG. 12C, the rostral-caudally positioned cathode electrodes E-1 and E-2 are shown as receiving 38% of the cathodic current –A, while the single medio-laterally positioned cathode electrode E-4 receives 24%. However, it is worth noting that the cathodic current fractionalization should not be arbitrary, and that experimentation or simulation may be necessary to promote or suppress activation as discussed above.

FIG. 12D shows a larger array 17, and illustrates that the cathode electrodes E-1 through E-4 do not need to be the nearest neighboring electrodes to the central anode electrode E+. In this example, the cathode electrodes E-1 through E-4 are spaced from the anode electrode E+ by an extra electrode. Further, although not shown, the cathode electrodes E-1 and E-4 do not need to be symmetrically positioned with respect to the anode electrode E+. For example, cathode electrodes E-3 and E-2 may be adjacent the anode electrode E+(as in FIG. 12A for example), while cathode electrodes E-1 and E-4 are spaced by one or more electrodes (as shown in FIG. 12D).

Figure 5:
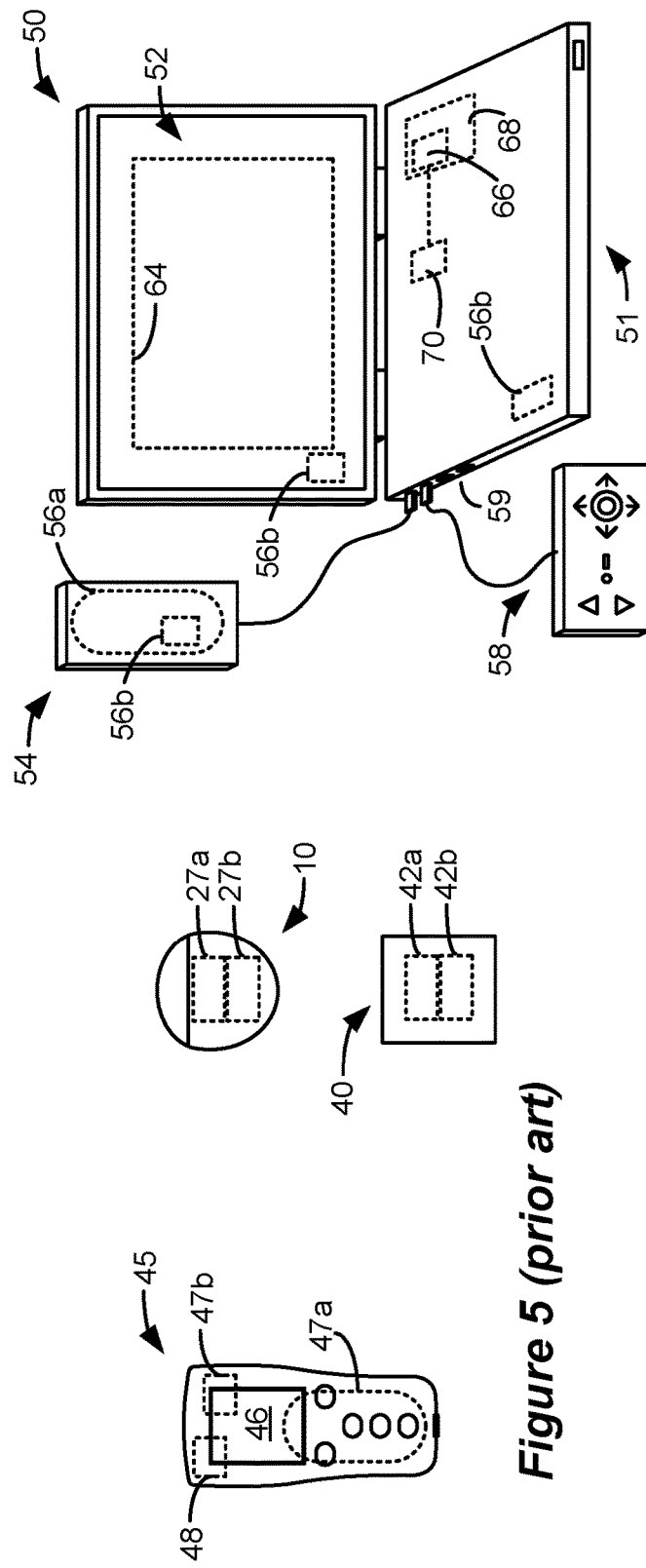
FIG. 5 shows various external devices capable of communicating with and programming stimulation in an IPG and ETS, in accordance with the prior art.
Figure 6:
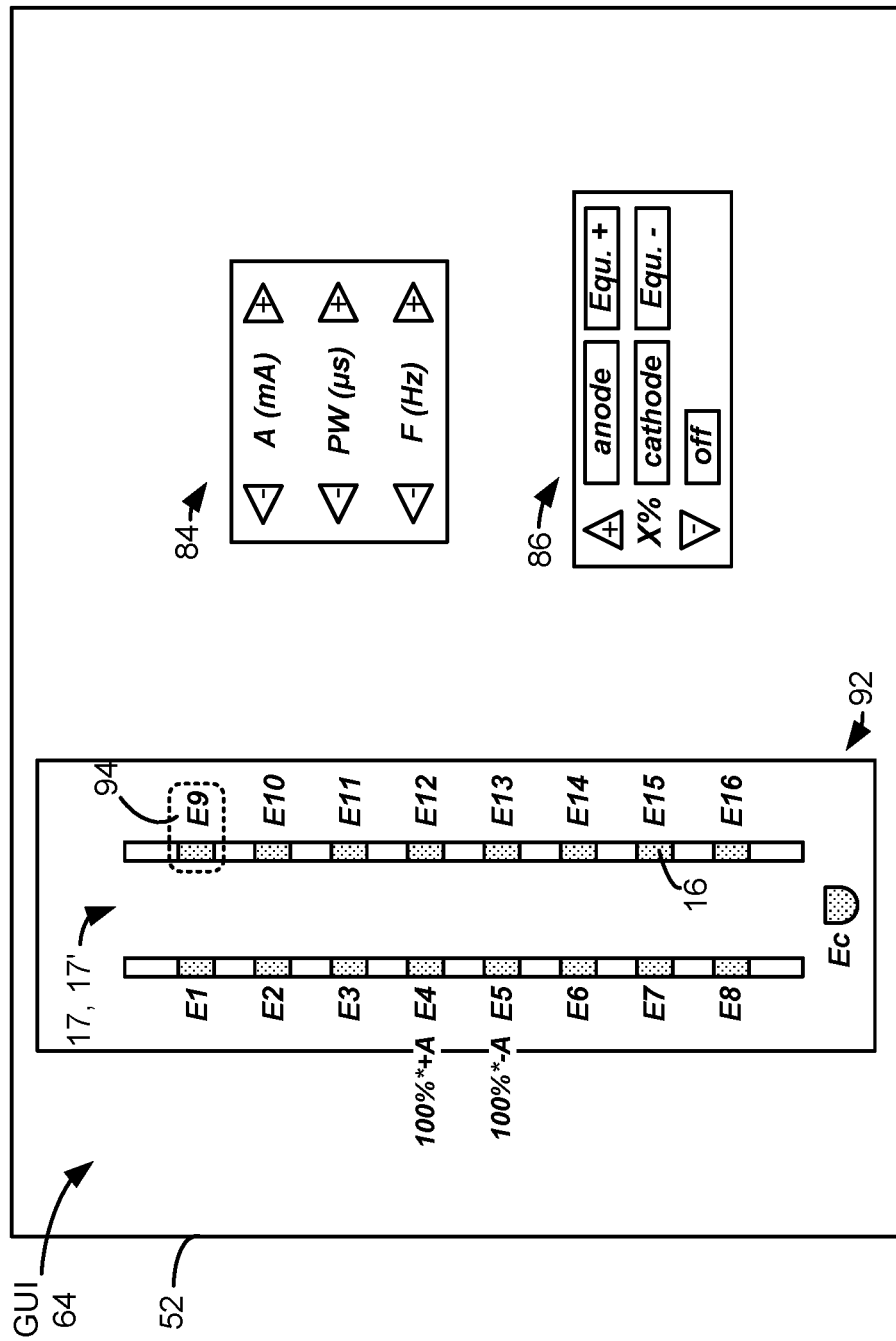
FIG. 6 shows a Graphical User Interface (GUI) of a clinician programmer external device for setting or adjusting stimulation parameters, in accordance with the prior art.
Figure 12E:
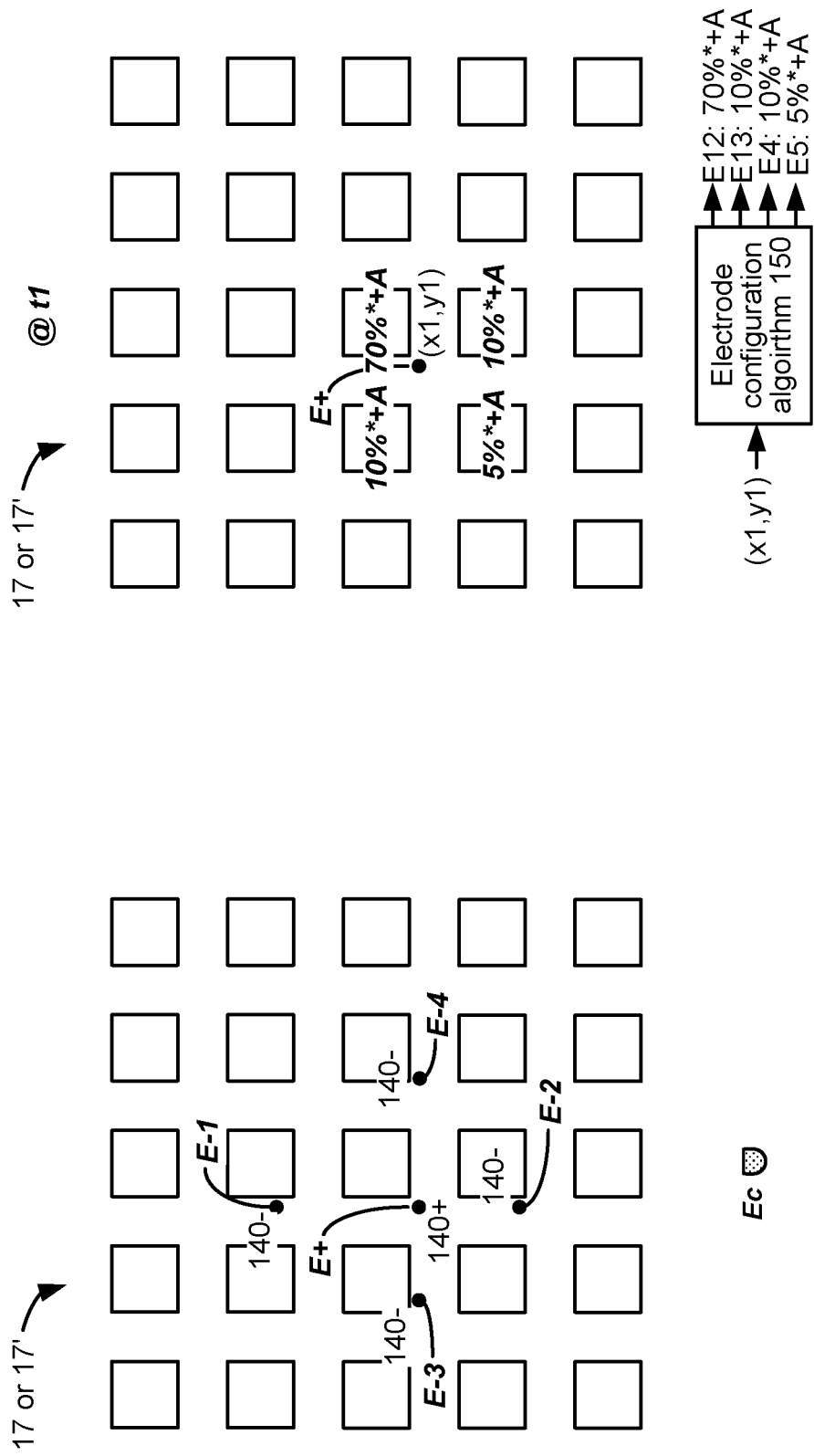

FIG. 12E shows that the anode electrode E+ can be formed as a virtual anode pole 140+ and cathode electrodes can be formed as virtual cathode poles 140—whose positions do not necessarily correspond to the positions of the physical electrodes 16 in the electrode array 17. In this regard, the patient or clinician can use a GUI 64 (FIG. 6) of the clinician programmer 50 or external controller 45 (e.g., FIG. 5) to define the positions of the virtual poles 140+ and 140− in the electrode array 17. When the position of a pole is set in the GUI, an electrode configuration algorithm 150 operating as software or firmware in the external device can compute what physical electrodes should be active, and with what polarities and current fractions, to best form the pole at the desired position. The reader is assumed familiar with this electrode configuration algorithm 150, and it is described further for example in U.S. Patent Application Publication 2019/0175915, which is incorporated herein by reference. An example of how the electrode configuration algorithm 150 can work is shown to the right in FIG. 12E, which shows formation of the virtual anode pole E+ 140+ during time t1. The position (x1,y1) of the virtual anode pole E+140+ is closest to electrode E12, somewhat close to electrodes E13 and E4, and generally neighboring electrode E5. As a result, the electrode configuration algorithm 150 may activate each of these electrodes during time t1, but may share the anodic current +A between them in different proportions (such as 70, 10, 10 and 5% respectively). The electrode algorithm 150 may likewise operate to define which physical electrodes should be active during time t2 to form the virtual cathode poles 140− at their respective positions, but this detail isn't shown.

Figure 12F:
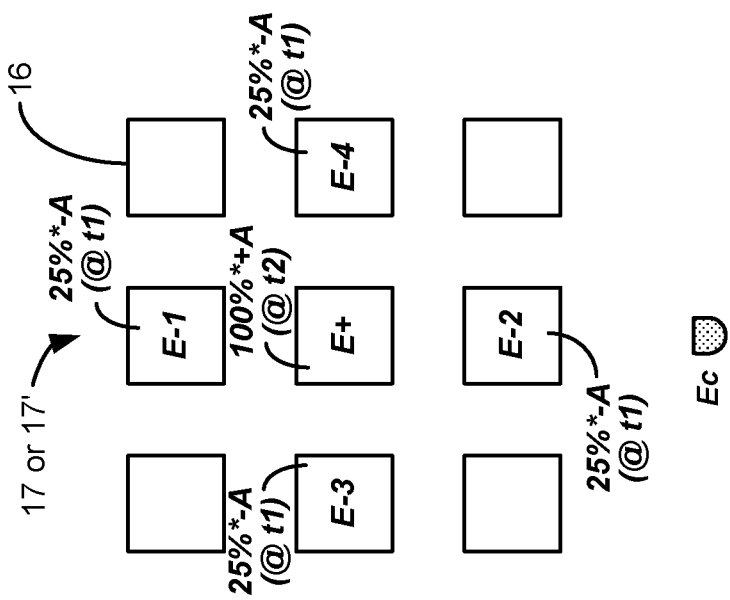

Lastly, FIG. 12F illustrates that the timing of the activation of the anodic and cathodic pulses can be reversed, with the cathodic pulses being activated at electrodes E-1 through E-4 at time t1, and the anodic pulse being activated at electrode E+ at time t2. This works the same effect, but stimulates the relevant fibers in the opposite order.

FIGS. 13A-13F show how the foregoing pulses can be moved in the electrode array 17. This is useful to provide stimulation over a wider range of neural tissue. The illustrated example uses the pulses as shows and described in FIG. 10, but any of the foregoing modifications of FIGS. 12A-12F could also be used.

Figures 13A, 13B:
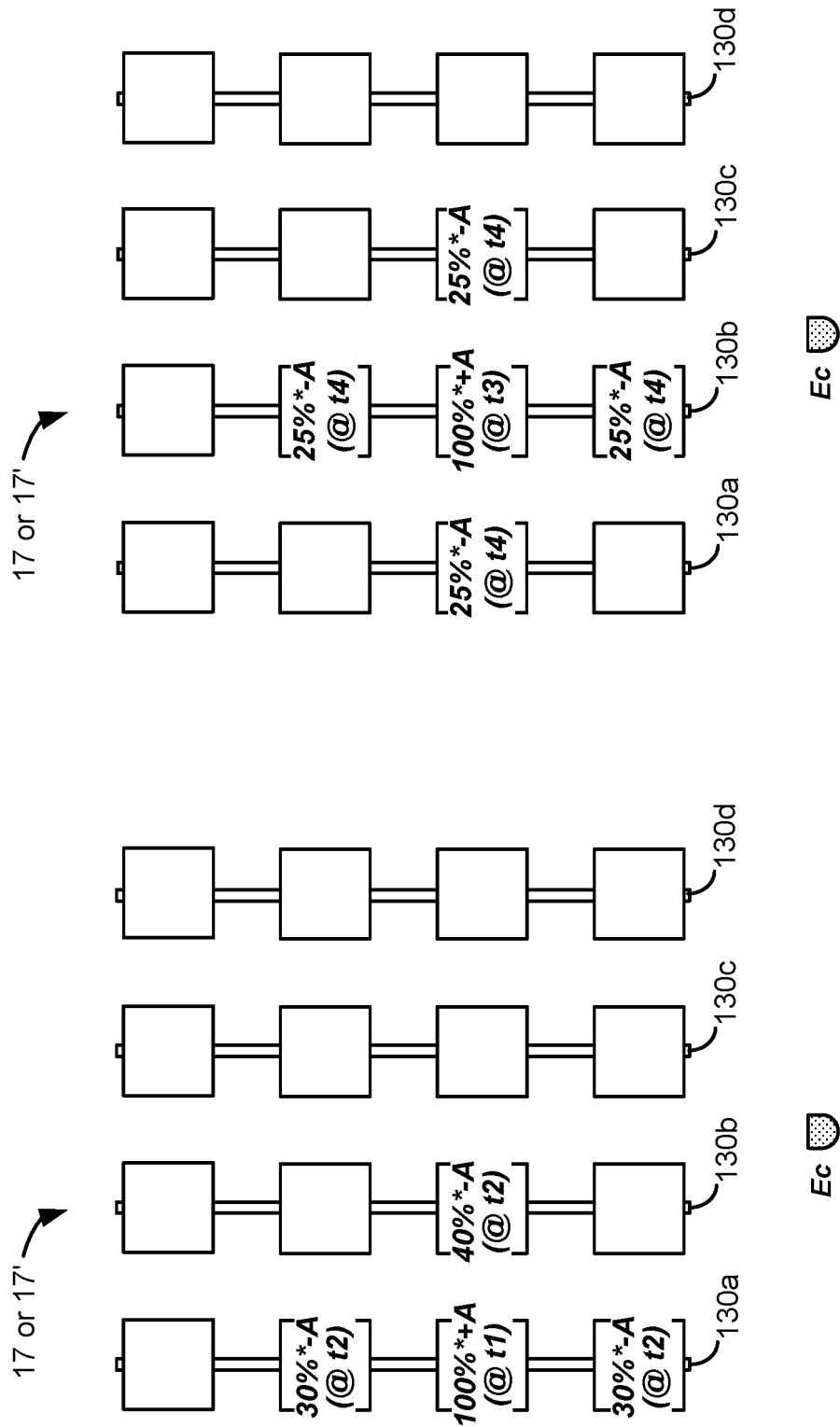
FIGS. 13A-13F show how the pulses may be moved through the electrode array to recruit or suppress recruitment of various dorsal column fibers.
Figures 13C, 13D:
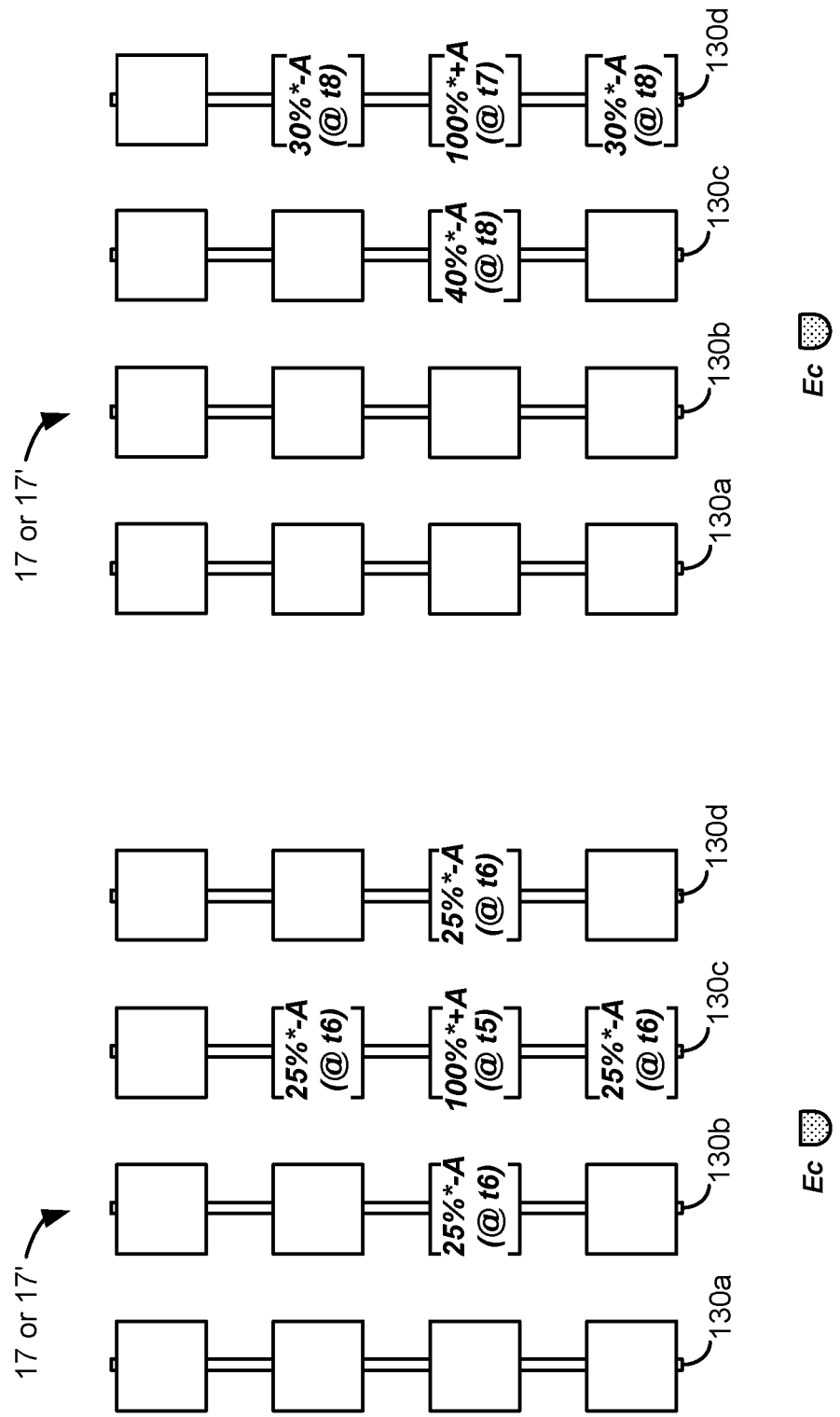
Figures 13E, 13F:
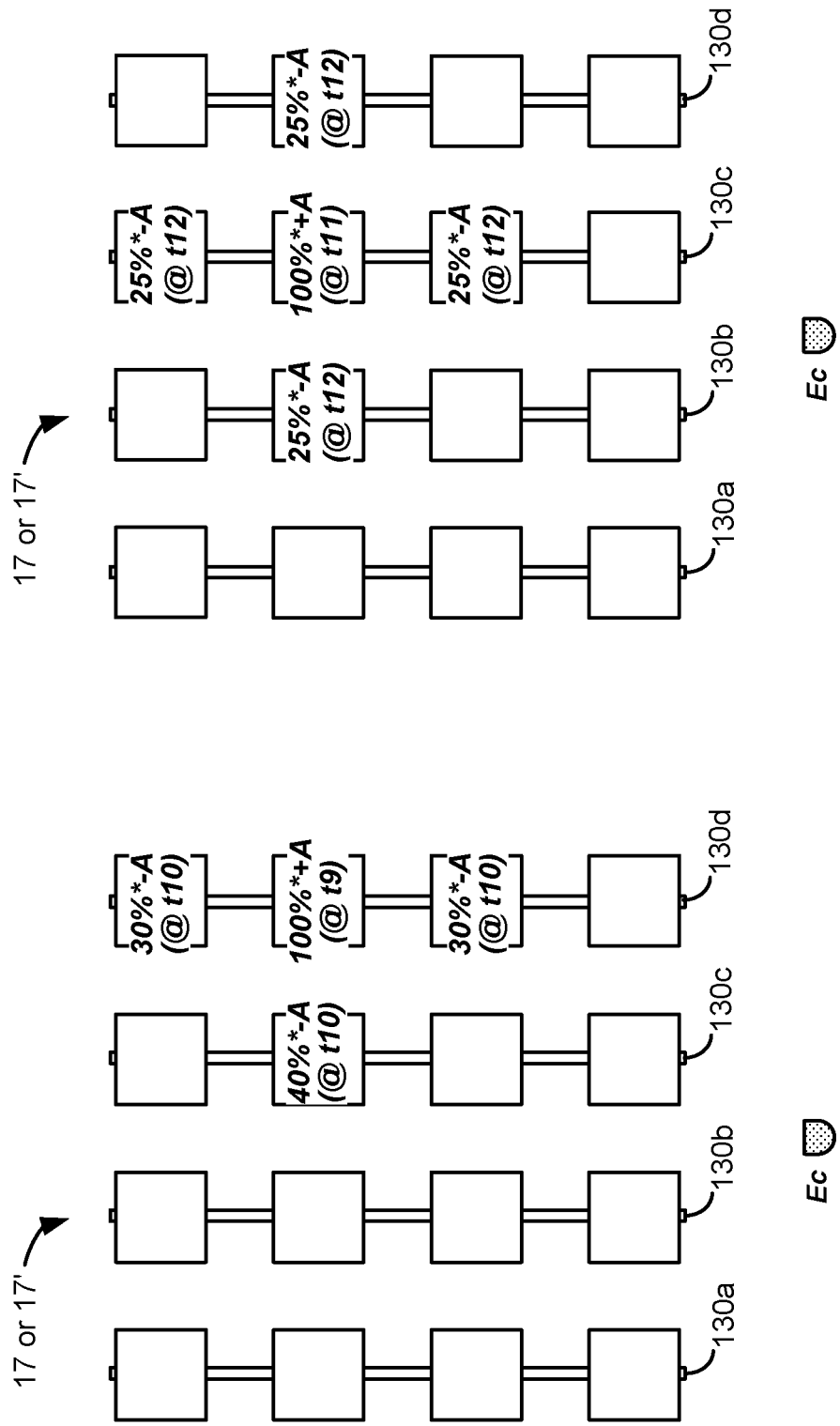

FIG. 13A shows the pulses applied at a left-most location in the electrode array 17, with the anode electrode placed at a left-most column in the array, and with an anodic pulse issued during time t1 (recruiting fibers 130a). Similar to what was illustrated in FIG. 12C, three cathode electrodes are used, with two placed rostro-caudally with respect to the anode electrode, and one placed medio-laterally to the right. These cathodic pulses are issued at time t2 (recruiting fibers 130b). In FIG. 13B, the active electrodes are shifted to the right, with the anodic pulse issued at time t3 (recruiting fibers 130b), and cathodic pulses issued at time t4 (recruiting fibers 130a and 130c). Notice that a fourth cathode electrode can now be accommodated to the left of the anode electrode. In FIG. 13C, the active electrodes are again shifted to the right, with the anodic pulse issued at time t5 (reciting fibers 130c), and cathodic pulses issued at time t6 (recruiting fibers 130b and 130d). In FIG. 13D, the active electrodes are shifted to the right, with the anode electrode placed at a right-most column in the array, and with an anodic pulse issued during time t7 (recruiting fibers 130d). Three cathode electrodes can again be used, with two placed rostro-caudally with respect to the anode electrode, and one placed medio-laterally to the left, with cathodic pulses issued during time t8 (recruiting fibers 130c). In FIG. 13E, the active electrodes are shifted upwards in the array (anodic at t9; cathodic at t10), and in FIG. 13F they are shifted to the left (anodic at t11 and cathodic at t12), and so on. In summary, the disclosed pulsing technique can be moved in the electrode array to recruit different dorsal column fibers at different times.

FIGS. 14A-14D show different anodic and cathodic pulses that can be used to selectively promote or suppress dorsal column recruitment. In these examples, a plurality of medio-laterally spaced electrodes are used in the array 17, such as the four electrodes E1-E4 shown in FIG. 14A, although three or more electrodes may also be used. These electrodes receive either anodic or cathodic pulses at different times t1-t4. In this example, electrode E1 receives a cathodic pulse at time t1, while electrodes E2-E4 receive anodic pulses. Although not shown, the cathodic pulse and anodic pulses may also be provided at pole locations in the array that do not necessarily correspond to the physical positions of the electrodes, similar to what was described earlier in FIG. 12E.

There are some differences compared to the examples provides earlier in FIGS. 10-13D. First, the cathodic pulses are larger in amplitude than the cathodic pulses. This is because recruitment largely occurs at the cathodic electrode, and thus fibers in the vicinity of 130a are recruited during time t1. The smaller amplitude anodic pulses at E2-E4 tend to suppress recruitment, and so fibers 130b-d are not recruited at time t1. The anodic pulses can also serve to "pre-pulse" fibers in these locations, as discussed further with respect to FIG. 14B. The cathodic pulse and the one or more anodic pulses may be formed in a single timing channel.

Figure 14A:
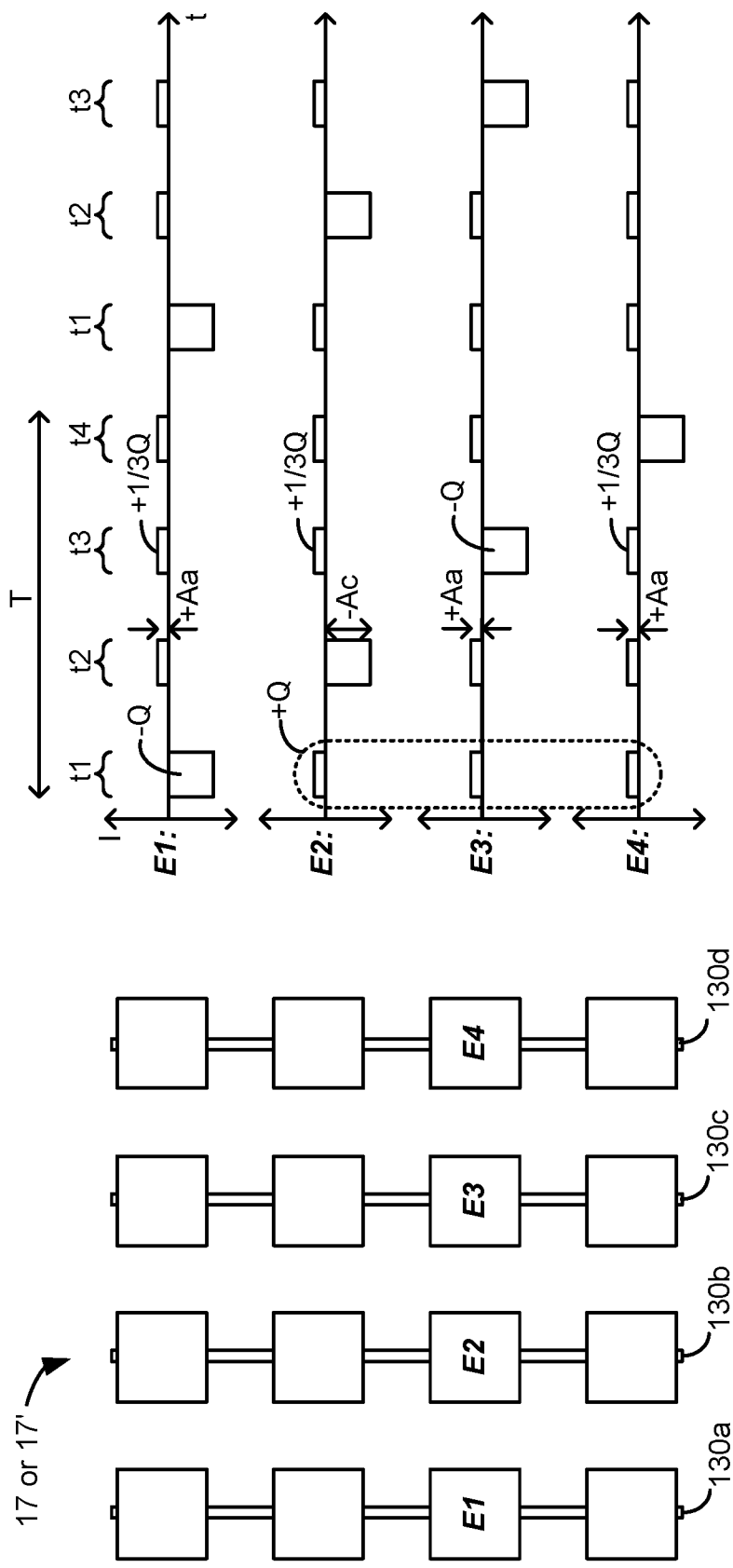
FIGS. 14A-14D show another example in which cathodic and anodic pulses can be used to recruit or suppress recruitment of various dorsal column fibers.

In the example of FIG. 14A, it may not be necessary to use the case electrode Ec. This is because the net current/charge at any point in time may be zero. For example, the amplitude of the cathodic pulse |Ac| may be three times the amplitude of the anodic pulses |Aa| Further, although not shown, the pulse widths of the cathodic and anodic pulses may be the same.

At time t2, the cathodic pulses moves to electrode E2, with electrodes E1, E3, and E4 comprising the cathodic pulses. This promotes recruitment of fibers 130b and tends to suppress recruitment of fibers 130a, 130c and 130d. The effect as the cathodic pulse moves to different electrodes (E3 at t3, and E4 at t4), is to selectively recruit different medio-laterally spaced fibers 130x at different times.

Note in this example that it is not necessary that the pulses have a charge recovery period (compares pulse phases 30a/b and 31a/b in FIG. 10). That is, the pulses may be monophasic. This is because the charge is naturally balanced at each electrode over time, i.e., over time period T which includes t1-t4. Take electrode E1 for example: the charge injected at t1 equals −Q, while the charge injected at t2-t4 equals in sum +Q. Hence neither active nor passive charge recovery is required, although it may also be used.

Figure 14B:
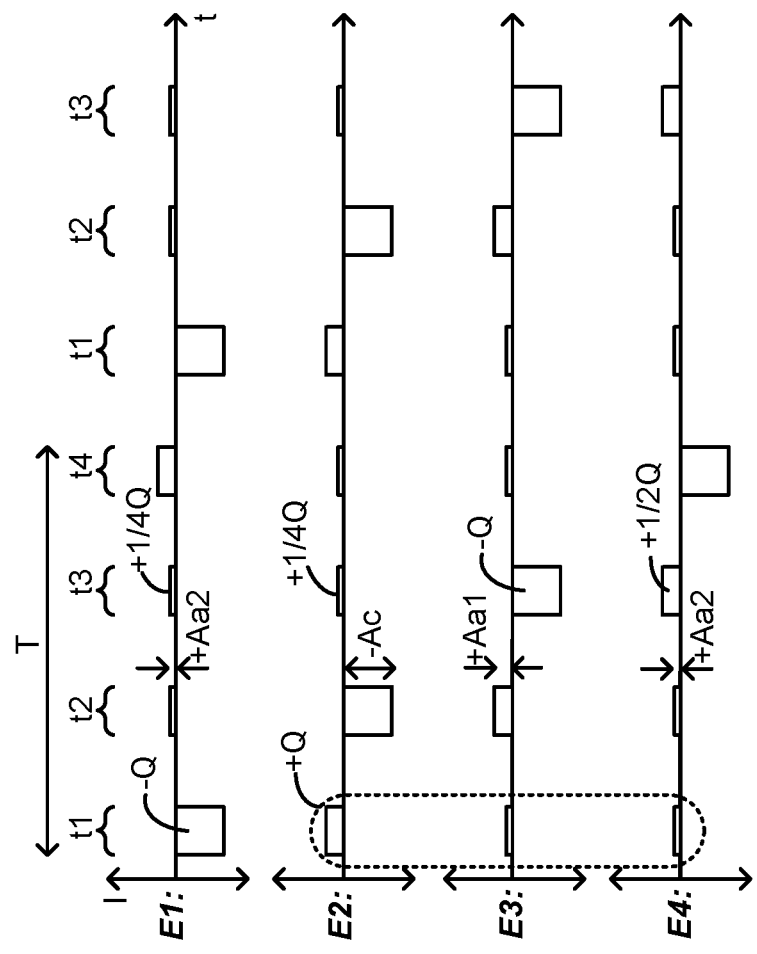
Figure 14B:
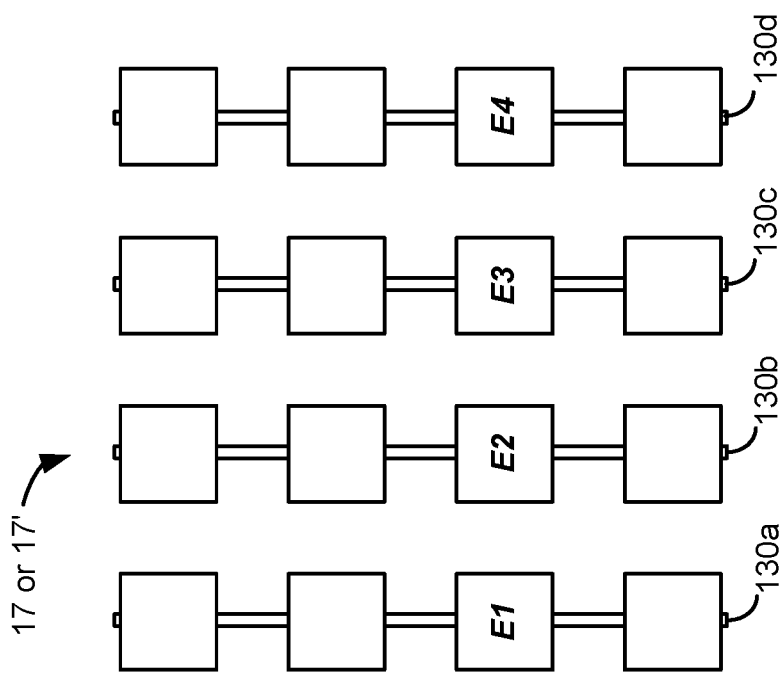

FIG. 14B provides a different example similar to FIG. 14B, except that the amplitudes of the anodic pulses are not equal at each of the electrodes at each time tx. For example, at time t1, the cathodic pulse of amplitude −Ac is applied to E1 at t1. Adjacent electrode E2 receives an anodic pulse of amplitude +Aa1, while electrodes E3 and E4 receive anodic pulses of amplitude +Aa2. In this example, Aa1=2*Aa2. Electrode E2 receives a higher amplitude pulse to "pre-pulse" the fibers 130b at this location. Pre-pulsing tends to make the fibers 130b at this location more susceptible to recruitment when they later receive a cathodic pulse, as occurs at time t2. At this time t2, the E2 received the cathodic pulse, while E3 now receives the anodic pre-pulse of amplitude Aa1. Electrodes E4 and E1 receive smaller anodic pulses of amplitude Aa2. This continues with the cathodic pulse being applied at a later time to the electrode that received the pre-pulse. That is, at t3, electrode E3 receives the cathodic pulse after receiving the pre-pulse at time t2; at t4 electrode E4 receives the cathodic pulse after receiving the pre-pulse at time t3, etc. Such pre-pulsing tends to promote recruitment by the later-applied cathodic pulse as previously mentioned. See, e.g., U.S. Patent Application Publication 2019/0298992 (describing pre-pulsing).

Similar to FIG. 14A, the pulses in FIG. 14B may be monophasic pulses not requiring charge recovery, because the charge is balanced at each electrode over the time period T. Further, the case electrode Ec may not be necessary as the net charge/current at any given time equals zero.

Figure 14C:
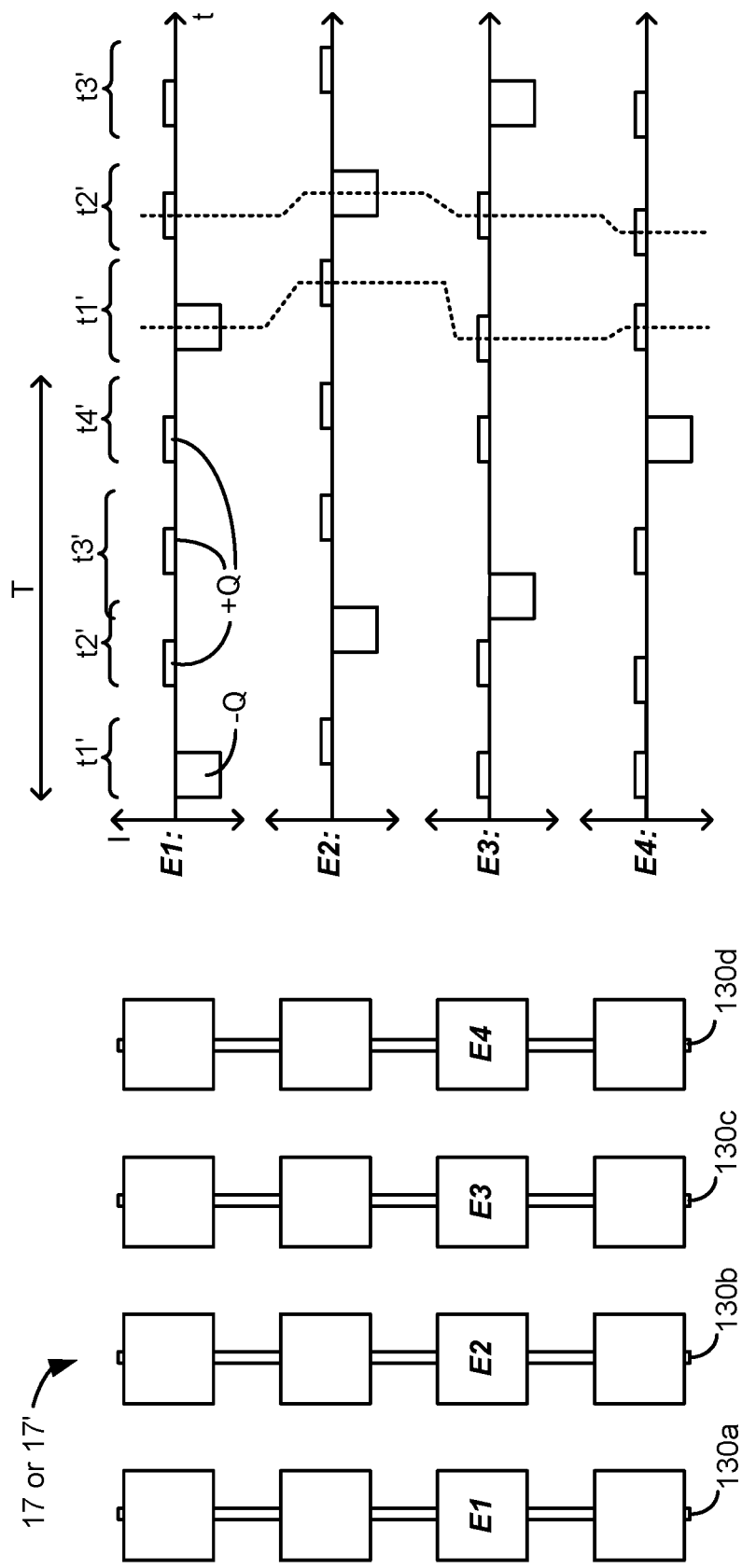
Figure 14D:
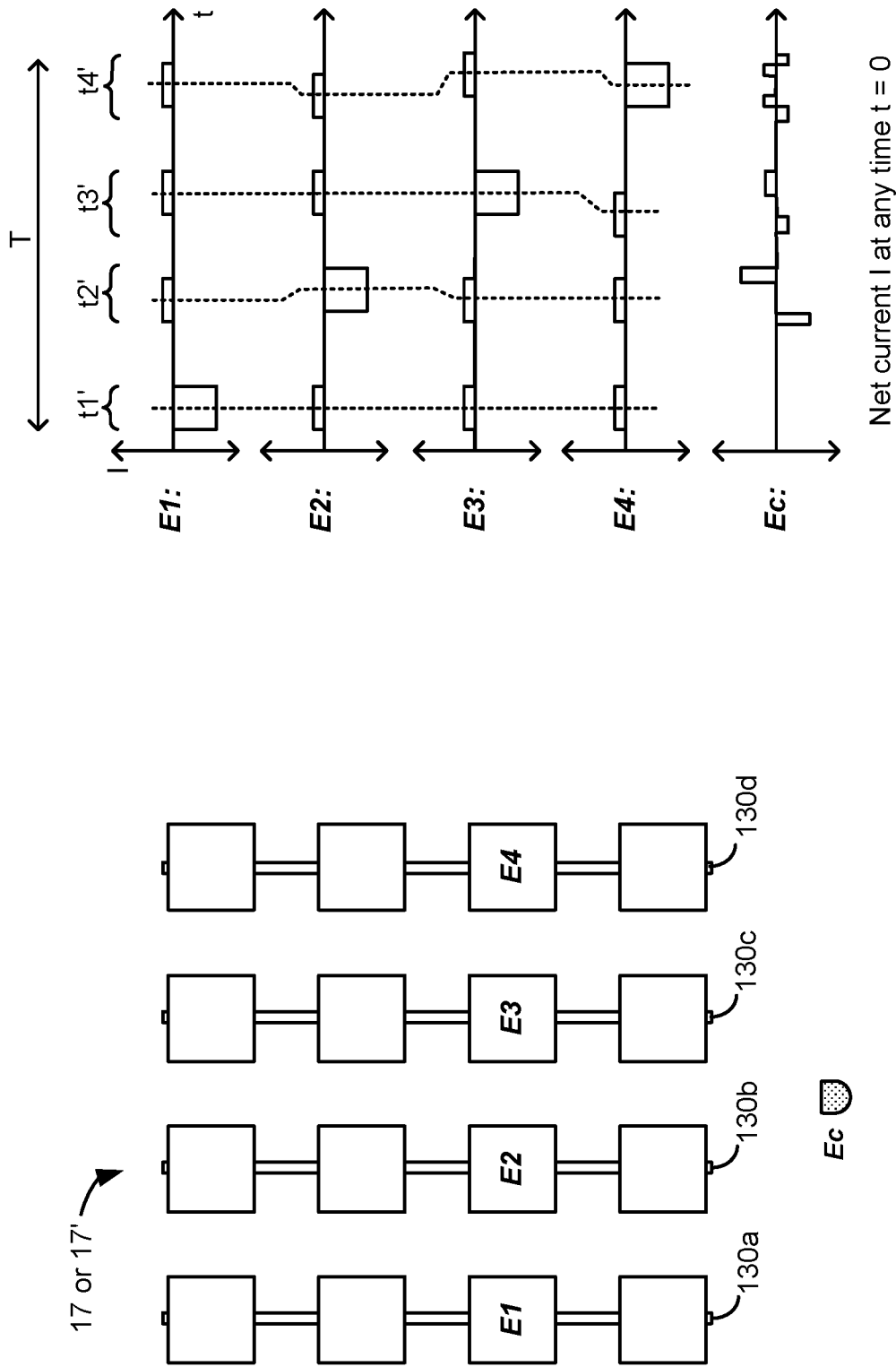

FIG. 14C shows another example similar to that shown in FIG. 14A, except that the timing of the pulses have been varied and essentially randomized. Thus, while pulses generally occur at time periods t1', t2', t3', and t4', these pulses do not strictly overlap during these periods. Further, the times periods may overlap, as occurs with time periods t2' and t3' for example. This example is useful because the stimulation provided to the tissue is not constant over each of the time periods tx', but instead can vary. This creates a number of different pole configurations at different points in time, and thus tends to recruit different medio-lateral populations of fibers. Notice that the charge can still be balanced at each electrode. Taking electrode E1 as an example, the charge is still balanced over time period T, with −Q injected during t1' and +Q injected in sum during t2'-t4'. In this example and given the different timings of the pulses during each period, it may be useful to form the pulses in different timing channels at each of the different electrode (pole) locations.

In FIG. 14C, there could be at certain points of time a non-zero net injection of charge/current into the tissue. This is not necessarily problematic, and can be useful to randomize recruitment. Still, in FIG. 14D, the case electrode Ec is used to balance the charge/current at any given point in time such that the net charge/current at any point in time is zero. As was the case with FIG. 14C, the pulses generally appear at time periods t1'-t4', although the pulses may not overlap during these periods. In this instance, current is provided to the case electrode Ec to net the current or charge at any given point in time to zero.

It should be noted that the examples of FIGS. 14A-14D can be varied in different ways. For example, although not shown, the pulse widths of the cathodic and anodic pulses do not all need to be equal. The amplitudes can also be varied. As one skilled will recognize, such variations can still occur while keeping the charge balanced at each electrodes, and while ensuring if desired that the net charge/current at any point in time is zero.

Instructions to form the various pulses as described can be stored in a computer-readable media associated with such devices, such as in a magnetic, optical, or solid state memory, such as those found in the IPG or ETS, or the external device (e.g., the clinician programmer) used to program the implant. The computer-readable media with such stored instructions may also comprise a device readable by the external device, such as in a memory stick or a removable disk, and may be wirelessly provided to the IPG or ETS. The computer readable media may reside elsewhere. For example, the computer-readable media may be associated with a server or any other computer device, thus allowing instructions to be downloaded to the clinician programmer system or external controller or to the IPG or ETS, via the Internet for example.

Note that while FIGS. 10-13F stress an approach involving use of a single anode pole (or electrode) and the use of flanking cathode poles (or electrodes), these polarities could also be reversed in other examples, and use a single cathode pole (or electrode) and flanking anode poles (or electrodes). Likewise, while FIGS. 14A-14D stress an approach using during each time period a single cathode pole (or electrode) and a plurality of medio-laterally aligned anode electrodes, these polarities could also be reversed in other examples, and use during each time period a single anode pole (or electrode) and a plurality of medio-laterally aligned cathode electrodes.

Note that some of the applications to which this present disclosure claims priority, which are incorporated by reference above, are directed to concepts (e.g., selecting optimal stimulation parameters, and in particular stimulation parameters that cause sub-perception at lower frequencies) that are relevant to the formation of anodic and cathodic pulses as described herein. Such anodic and cathodic pulses can also be used in the context of these priority applications.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming a spinal cord stimulator device implanted in a patient's tissue, the spinal cord stimulator device comprising a conductive case electrode and coupled to an electrode array comprising a plurality of electrodes, the method comprising:
   programming the spinal cord stimulator device to provide anodic pulses at a frequency at an anodic pole at a first position in the electrode array during first durations;
   programming the spinal cord stimulator device to provide a plurality of cathodic pulses at the frequency at cathodic poles at second positions in the electrode array different from the first position during second durations interleaved with the first durations; and
   programming the spinal cord stimulator device to provide a cathodic charge recovery pulse at the anodic pole after each of the anodic pulses, and programming the spinal cord stimulator device to provide anodic charge recovery pulses at the cathodic poles after each of the cathodic pulses,
   wherein no cathodic pulses are provided to the electrode array during the first durations.

2. The method of claim 1, wherein no anodic pulses are provided to the electrode array during the second durations.

3. The method of claim 1, wherein the first and second durations do not overlap in time.

4. The method of claim 1, wherein the case electrode provides a cathodic current return for the anodic pulses during the first durations, and wherein the case electrode provides an anodic current return for the cathodic pulses during the second durations.

5. The method of claim 1, wherein the anodic pulses are programmed in a first timing channel in the spinal cord stimulator device, and wherein the cathodic pulses are programmed in a second timing channel in the spinal cord stimulator device.

6. The method of claim 1, wherein a charge of the anodic pulse during one of the first durations is equal but opposite of the sum of a charge of the cathodic pulses during one of the second durations.

7. The method of claim 1, wherein an amplitude of the anodic pulse during one of the first durations is equal to a sum of the amplitudes of the cathodic pulses during one of the second durations.

8. The method of claim 1, wherein the amplitudes of the cathodic pulses are equal.

9. The method of claim 1, wherein at least two of the cathodic poles are aligned rostral-caudally in the electrode array with respect to the anodic pole.

10. The method of claim 9, wherein at least one of the cathodic poles is aligned medio-laterally in the electrode array with respect to the anodic pole.

11. The method of claim 1, wherein the case electrode is further programmed with a cathodic pulse during the second durations.

12. The method of claim 1, wherein the case electrode is further programmed with an anodic pulse during the first durations.

13. The method of claim 1, further comprising calibrating an amplitude of the anodic pulses, the cathodic pulses, or both of the anodic pulses and the cathodic pulses, so as to elicit a response in the tissue.

14. The method of claim 13, wherein both the anodic pulses and the cathodic pulses are calibrated so as to elicit a response in the tissue.

15. The method of claim 13, wherein the amplitude is calibrated so as to elicit a response in the patient's tissue using feedback from the patient.

16. The method of claim 13, wherein the amplitude is calibrated so as to elicit a response in the patient's tissue using measurements of neural responses in the patient's tissue.

17. A spinal cord stimulator device configured for implantation in a patient's tissue, comprising:
  a conductive case electrode;
  an electrode array comprising a plurality of electrodes; and
  control circuitry configured to:
    provide anodic pulses at a frequency at an anodic pole at a first position in the electrode array during first durations;
    provide a plurality of cathodic pulses at the frequency at cathodic poles at second positions in the electrode array different from the first position during second durations interleaved with the first durations; and
    provide a cathodic charge recovery pulse at the anodic pole after each of the anodic pulses, and to provide anodic charge recovery pulses at the cathodic poles after each of the cathodic pulses,
  wherein no cathodic pulses are provided to the electrode array during the first durations.

* * * * *